(12) United States Patent
Jiang et al.

(10) Patent No.: US 11,628,285 B2
(45) Date of Patent: *Apr. 18, 2023

(54) NEPHROSTOMY TUBE

(71) Applicant: Ningbo First Hospital, Ningbo (CN)

(72) Inventors: Junhui Jiang, Ningbo (CN); Zejun Yan, Ningbo (CN); Yue Cheng, Ningbo (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/820,238

(22) Filed: Aug. 16, 2022

(65) Prior Publication Data

US 2022/0387771 A1    Dec. 8, 2022

Related U.S. Application Data

(63) Continuation of application No. 17/576,967, filed on Jan. 16, 2022, now Pat. No. 11,446,476.

(30) Foreign Application Priority Data

May 8, 2021   (CN) .......................... 202110502083.4
May 8, 2021   (CN) .......................... 202110502093.8

(51) Int. Cl.
*A61M 27/00*   (2006.01)
*A61M 25/00*   (2006.01)
*A61M 25/10*   (2013.01)

(52) U.S. Cl.
CPC ...... *A61M 27/008* (2013.01); *A61M 25/0043* (2013.01); *A61M 25/10* (2013.01); *A61M 2025/006* (2013.01)

(58) Field of Classification Search
CPC ............ A61M 27/008; A61M 25/0043; A61M 25/10; A61M 2025/006; A61M 2210/1078; A61M 2210/1082; A61M 2210/1085; A61M 25/0068; A61M 25/007; A61M 2025/0073
See application file for complete search history.

(56) References Cited

U.S. PATENT DOCUMENTS 2,614,563 A * 10/1952 Devine, Jr. ........... A61M 31/00
                                                          604/45
3,528,427 A *  9/1970 Sheridan ............... A61M 27/00
                                                          604/45

(Continued)

*Primary Examiner* — Adam Marcetich
(74) *Attorney, Agent, or Firm* — Tsz Lung Yeung

(57) ABSTRACT

The present disclosure discloses a nephrostomy tube and a nephrostomy tube with curved drainage. The nephrostomy tube with curved drainage includes a bending head, a balloon element, and an elongated main body integrally connected with each other, wherein the nephrostomy tube with curved drainage has an guiding channel adapted for a guiding member to penetrate through, wherein the bending head has a first inner channel and at least two drainage bending channels located on the outer side of the first inner channel, wherein the balloon element has an air chamber and a second inner channel, wherein the at least two drainage bending channels are communicated with the second inner channel, wherein the elongated main body has a third inner channel communicated with the second inner channel of the balloon element, wherein the first inner channel, the second inner channel and the third inner channel from the guiding channel.

20 Claims, 29 Drawing Sheets

(56) References Cited

U.S. PATENT DOCUMENTS

| | | | | |
|---|---|---|---|---|
| 4,182,343 | A | * | 1/1980 | Inaba .................... A61M 27/00 |
| | | | | 604/268 |
| 4,307,723 | A | | 12/1981 | Finney |
| 4,610,663 | A | | 9/1986 | Rosenberg |
| 4,787,892 | A | | 11/1988 | Rosenberg |
| 5,116,310 | A | | 5/1992 | Seder |
| 5,360,414 | A | | 11/1994 | Yarger |
| 6,478,789 | B1 | | 11/2002 | Spehalski |
| 6,796,976 | B1 | | 9/2004 | Chin |
| D558,338 | S | * | 12/2007 | Itoh ............................ D24/112 |
| 2004/0006331 | A1 | | 1/2004 | Shchervinsky |
| 2004/0176745 | A1 | | 9/2004 | Ferguson |
| 2004/0249360 | A1 | | 12/2004 | Spehalski |
| 2007/0270888 | A1 | | 11/2007 | Barrientos |
| 2008/0312578 | A1 | * | 12/2008 | DeFonzo ............ A61M 39/284 |
| | | | | 604/6.16 |
| 2009/0221992 | A1 | | 9/2009 | Hannon |
| 2010/0056988 | A1 | | 3/2010 | Nishtala |
| 2013/0281985 | A1 | | 10/2013 | Querol Garcia |
| 2013/0345679 | A1 | | 12/2013 | Garon |
| 2014/0121590 | A1 | | 5/2014 | Degen |
| 2014/0228734 | A1 | * | 8/2014 | Wilson .............. A61M 25/0071 |
| | | | | 604/8 |
| 2014/0276662 | A1 | | 9/2014 | Douglas |
| 2015/0018802 | A1 | | 1/2015 | Zvuloni |
| 2018/0207014 | A1 | | 7/2018 | Rousseau |
| 2019/0105465 | A1 | | 4/2019 | Erbey, II |

* cited by examiner

NEPHROSTOMY TUBE

CROSS REFERENCE OF RELATED APPLICATION

This is a Continuation application that claims the benefit of priority under 35 U.S.C. § 119 to a non-provisional application, application Ser. No. 17/576,967, filed date 01/16/2022, which is a non-provisional application that claims the benefit of foreign priority to two Chinese applications, application number 2021105020938 filed Date 05/08/2021 and application number 2021105020834 filed Date 05/08/2021.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to medical devices, and more particular to a nephrostomy tube and a nephrostomy tube with curved drainage.

Description of Related Arts

Nephrostomy drainage surgery is a surgery that punctures or incises the renal parenchyma so that a guiding tube for draining urine, pus, blood, etc., can be inserted into the renal pelvis and also facilitates the formation of the sinus tract. In the nephrostomy drainage surgery, a nephrostomy tube is commonly required to be disposed in the nephrostomy channel for a predetermined time.

The main body of the existing nephrostomy tube has a channel therein, and also has two symmetrical holes formed at the two opposed end portions thereof which are communicated with the internal channel, wherein when one end portion of the main body is disposed and retained in the renal pelvis, the fluid in the renal pelvis is sent out through the delivery path formed by the two holes and the internal channel.

As mentioned above, the fluids that nephrostomy drainage drains are urine, pus, blood, etc., whose concentration are much larger than that of ordinary body fluids, such as urine, and there are even some small lumps within the fluids. In this case, it has been found in practice that the existing nephrostomy tube is often blocked, which brings a lot of inconvenience to both doctors and patients.

On the one hand, if this blockage is not discovered in time, it may cause excessive kidney pressure and cause complications for the patients, and if it is clogged frequently, flushing or replacing the pipeline is also relatively troublesome. On the other hand, for medical staff, they need to put more energy and time to observe and control so as to avoid blockages, and to deal with blockages in time if necessary.

On the one hand, if this blockage is not discovered in time, it may cause excessive kidney pressure and cause complications for the patients, and if it is clogged frequently, flushing or replacing the pipeline is also relatively troublesome. On the other hand, for medical staff, they need to put more energy and time to observe and control so as to avoid blockages, and to deal with blockages in time if necessary.

Moreover, the end portion of the existing nephrostomy tube is straight, and the hole formed thereat for allowing the fluid to enter the channel has a relatively small size. In other words, there is only one through hole that guides the fluids to the drainage path, which is very limited and is the root cause of its prone to blockage.

In many current treatment schemes, the nephrostomy tube 771P is commonly utilized for diversion in order to assist the patient to recover as soon as possible after the surgery, as shown in FIG. 1. For example, in a percutaneous nephrolithotomy surgery, the nephrostomy tube 771P is disposed and retained in the renal pelvis for drainage, and also the nephrostomy tube plays a role of compression and hemostasis if bleeding occurs during or after the operation.

The existing nephrostomy tube 771P is generally a hollow tube made of medical rubber, and its front end is provided with a through hole 7710P for allowing external liquid into the fistula tube 771P therethrough and then the fluid is drained outside through the nephrostomy tube 771P. Also an airbag is provided at the front end for compression and hemostasis.

In practice, the normal drainage function of the existing nephrostomy tube 771P rely on the through hole 7710P formed at the front end of the tube, which is disposed within the body, and the opening formed at the rear end of the tube outside the body. Obviously, if the through hole 7710P at the front end is blocked, the entire nephrostomy tube 771P will lose its function. For instance, for the bladder nephrostomy tube 771P, if the bladder nephrostomy tube 771P is blocked or compressed, the pressure in the bladder will exceed the safe pressure or cause hydronephrosis or upper urinary tract function damage.

When the drainage of the nephrostomy tube 771P is not smooth or blocked, the general solution is to bend the nephrostomy tube 771P or repeatedly squeeze the nephrostomy tube 771P so as to use the fluid within the nephrostomy tube 771P to reversely impacts the through hole 7710P at the front end of the nephrostomy tube 771P. Although such solution has a certain effect, due to the natural defects in the design of the nephrostomy tube 771P, it cannot effectively solve the blockage problem every time. In actual use, a larger blood clot may wrap the entire front end portion of the nephrostomy tube 771P, thereby causing the through holes 7710P formed at the front end portion to lose its drainage function, as shown in FIG. 1 of the drawings.

SUMMARY OF THE PRESENT INVENTION

The invention is advantage in that it provides a nephrostomy tube, wherein the nephrostomy tube is provided with a plurality of drainage inlets, such that even if one of the drainage inlets is blocked, the other drainage inlets can still continue to work normally. In particular, the drainage inlets are not arranged in a same flat surface in such a manner that the risk of all the drainage inlets being blocked together can be substantially reduced.

Another advantage of the invention is to provide a nephrostomy tube, wherein the nephrostomy tube is provided with at least one guiding groove to extend the flowing distance of the fluid on the outer surface thereof, such that blockage of being concentrated on a certain position on the outer surface of the nephrostomy tube can be effectively prevented.

Another advantage of the invention is to provide a nephrostomy tube, wherein each of the drainage inlets is corresponding to each guiding groove respectively, in such a manner that the probability of clogging at all the drainage inlets can be reduced through the guiding grooves.

Another advantage of the invention is to provide a nephrostomy tube, wherein the guiding groove is capable of separating easily-clogged unwanted objects so as to minimize the unwanted objects, while playing a drainage role, thereby effectively preventing all the drainage inlets being blocked.

Another advantage of the invention is to provide a nephrostomy tube with curved drainage, which guides fluids into the nephrostomy tube by extending the drainage path via a bending drainage manner, so that it is not limited to enter into the inner space of the nephrostomy tube only through a through hole formed at the front end thereof.

Another advantage of the invention is to provide a nephrostomy tube with curved drainage, wherein the nephrostomy tube allows fluids in the renal pelvis enter the nephrostomy tube from multiple directions in an open drainage manner, instead of being limited to one direction specified by the one through hole formed at the front end of the nephrostomy tube.

Another advantage of the invention is to provide a nephrostomy tube with curved drainage which adopts an open drainage method to guide the fluids, which is more suitable for dense fluids or viscous fluids or fluids containing small pieces, and is more suitable for being used after a nephrostomy drainage surgery.

Another advantage of the invention is to provide a nephrostomy tube with curved drainage, which is provided with a plurality of drainage bending channels which are arranged at intervals to divert the fluids so as to reduce the occurrence of clogging.

Another advantage of the invention is to provide a nephrostomy tube with curved drainage which disperses the accumulated liquid and particulate matters through a plurality of guiding walls, so as to reduce the probability that the fluid with particulate matters accumulates in one location, and therefore the occurrence of the nephrostomy tube being completely blocked can be reduced.

Another advantage of the invention is to provide a nephrostomy tube with curved drainage which comprises a bending head which is bent when the nephrostomy tube is disposed within the human body, In particular, the bent bending head do not have any sharp points or protruding portions so as to reduce the adverse stimulating effect on human internal organs.

Another advantage of the invention is to provide a nephrostomy tube with curved drainage which coordinates the functions of bending and drainage guiding by designing the opening positions of the drainage bending channels and the bending direction of the bending head.

Another advantage of the invention is to provide a nephrostomy tube with curved drainage, wherein, in one embodiment of the present invention, the nephrostomy tube comprises an outer wall which is arranged at the outer end of the guiding wall to prevent the outer end of the guide wall from directly contacting the inner membrane of the human body, so that the bending head can pass smoothly along the passage of the human body.

Another advantage of the invention is to provide a nephrostomy tube with curved drainage, wherein the outer walls are arc-shaped covering the outside of the guiding walls, and there is a gap defined between the adjacent two outer walls, such that the guiding walls can form protective guiding walls in a substantially circular shape while ensuring a smooth drainage.

According to one aspect of the present invention, it provides a nephrostomy tube with curved drainage, which comprises:

a bending head;

a balloon element;

An elongated main body, wherein the bending head, the balloon element and the elongated main body are integrally connected with each other, wherein the nephrostomy tube with curved drainage has an guiding channel adapted for a guiding member to penetrate through, wherein the bending head has a first inner channel and at least two drainage bending channels located on the outer side of the first inner channel, wherein the balloon element has an air chamber and a second inner channel, the air chamber is circumferentially formed on the outer side of the second inner channel, wherein the at least two drainage bending channels are communicated with the second inner channel, wherein the elongated main body has a third inner channel communicated with the second inner channel of the balloon element, wherein the first inner channel, the second inner channel and the third inner channel from the guiding channel In one embodiment of the present invention, each of the drainage bending channels has an opening communicated to the external and a communication hole communicated with the second inner channel of the balloon element.

In one embodiment of the present invention, the nephrostomy tube with curved drainage further comprises a first tubular body and a plurality of guiding walls radially extended on the outer side of the first tubular body, wherein each adjacent two guiding walls form one of the drainage bending channels.

In one embodiment of the present invention, the nephrostomy tube with curved drainage further comprises a first tubular body and a plurality of guiding walls symmetrically distributed around the outer side of the first tubular body.

In one embodiment of the present invention, each of the guiding walls has a micro hole configured for communicating the adjacent two drainage bending channels.

In one embodiment of the present invention, the bending head has a tapering end portion.

In one embodiment of the present invention, the nephrostomy tube with curved drainage further comprises a positioning line extending along the elongated main body.

In one embodiment of the present invention, the bending head comprises a protective wall curvedly extended on the outer side of the guiding walls, wherein a gap, communicating the external space and the inner space of the drainage bending channels, is defined between each adjacent two protective walls.

In one embodiment of the present invention, one of the drainage bending channels is provided on the inner side of the bending head, while another one of the drainage bending channels is provided on the outer side of the one the of the drainage bending channels.

In one embodiment of the present invention, there are two, or three, or four, or five, or six, or seven guiding walls are provided.

According to another aspect of the present invention, it further provides a nephrostomy tube, comprising a tubular main body and a marking line, and having at least two guiding grooves and a drainage channel, wherein the tubular main body comprises a front section and a rear section, wherein the drainage channel is penetrated through the rear section and is located inside the rear section, the front section has an outer surface and at least a portion of the outer surface is indented to define the at least two guiding grooves, and each of the at least two guiding grooves is communicated with the drainage channel, wherein each of the at least two guiding grooves has a drainage starting end and a drainage ending end, wherein the drainage ending end is closer to the rear section with respective to the drainage starting end, and at least one of the drainage starting end and at least one of the drainage ending end of the two adjacent guiding grooves have a height difference, wherein the marking line is adapted for indicating the position of the tubular main body.

In one embodiment of the present invention, the front section of the nephrostomy tube is bent to form a bending portion, wherein the at least two guiding grooves are provided at the bending portion and curvedly extended along the bending portion.

In one embodiment of the present invention, the bending portion has a bending front side and a bending back side, wherein the bending front side is a side that the front section is bent towards, while at least one of the at least two guiding grooves is provided at the bending back side of the bending portion.

In one embodiment of the present invention, the guiding groove that provided at the bending back side of the bending portion is longest.

In one embodiment of the present invention, there are three or more than three guiding grooves provided, and the drainage ending end of each of the guiding grooves is configured in step-shaped.

In one embodiment of the present invention, the tubular main body further has an installation channel adapted for installing a mounting member therethrough, wherein the tubular main body is capable of being guided to a predetermined position with the guidance of the mounting element.

In one embodiment of the present invention, the nephrostomy tube further comprises a pillar member and at least two supporting walls outwardly and radially extended from the pillar member to form the guiding grooves, wherein the pillar member and the supporting walls form at least a portion of the front section.

In one embodiment of the present invention, the nephrostomy tube further comprises a pillar member and at least two supporting walls outwardly and radially extended from the pillar member to form the guiding grooves, wherein the pillar member and the supporting walls form at least a portion of the front section and the installation channel is penetrated through the front section.

In one embodiment of the present invention, the nephrostomy tube further comprises an airbag element and has an air channel, wherein the airbag element is provided at the rear section of the tubular main body and is communicated with the air channel, such that the airbag element can be inflated through the air channel, wherein the tubular main body further comprises a charging port communicated with the air channel.

In one embodiment of the present invention, the front section of the nephrostomy tube is bent to form a bending portion, wherein the at least two guiding grooves are provided at the bending portion and curvedly extended along the bending portion, wherein the bending portion has a bending front side and a bending back side, wherein the bending front side is a side that the front section is bent towards, while at least one of the at least two guiding grooves is provided at the bending back side of the bending portion, wherein the guiding groove that provided at the bending back side of the bending portion is longest, wherein there are three or more than three guiding grooves provided, and the drainage ending end of each of the guiding grooves is configured in step-shaped, wherein the tubular main body further has an installation channel adapted for installing a mounting member therethrough, wherein the tubular main body is capable of being guided to a predetermined position with the guidance of the mounting element, wherein the nephrostomy tube further comprises a pillar member and at least two supporting walls outwardly and radially extended from the pillar member to form the guiding grooves, wherein the pillar member and the supporting walls form at least a portion of the front section, and the installation channel is penetrated through the front section, wherein the nephrostomy tube further comprises an airbag element and has an air channel, wherein the airbag element is provided at the rear section of the tubular main body and is communicated with the air channel, such that the airbag element can be inflated through the air channel, wherein the tubular main body further comprises a charging port communicated with the air channel, wherein the front section has a front-section head end and an opposing front-section tail end, the rear section has a rear-section front end and an opposing rear-section tail end, wherein the front-section tail end of the front section is coupled to the rear-section front end of the rear section, and at least one drainage ending end of at least one of the guiding grooves is far away from the front-section tail end, wherein the tubular main body further has a drainage inlet provided at the front section of the tubular main body and communicated with the guiding grooves and the drainage channel, wherein the drainage inlets is provided at the rear-section head end of the rear section along its length direction or is provided at the pillar member.

These and other objectives, features, and advantages of the present invention will become apparent from the following detailed description, the accompanying drawings, and the appended claims.

DETAILED DESCRIPTION OF THE PREFERRED EMBODIMENT

Figure 1:
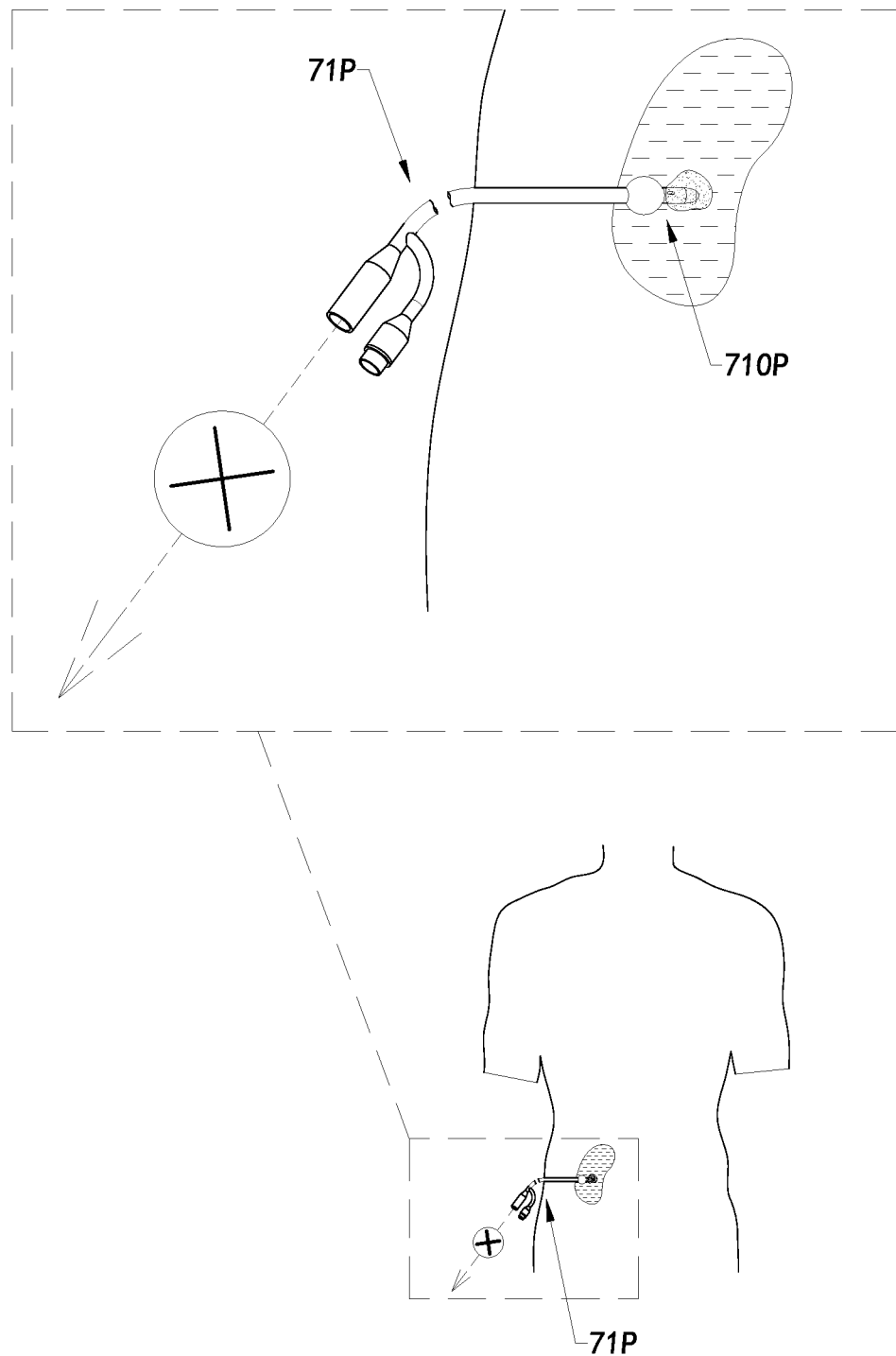
FIG. 1 is a schematic view of a conventional nephrostomy tube during its use.
Figure 2A:
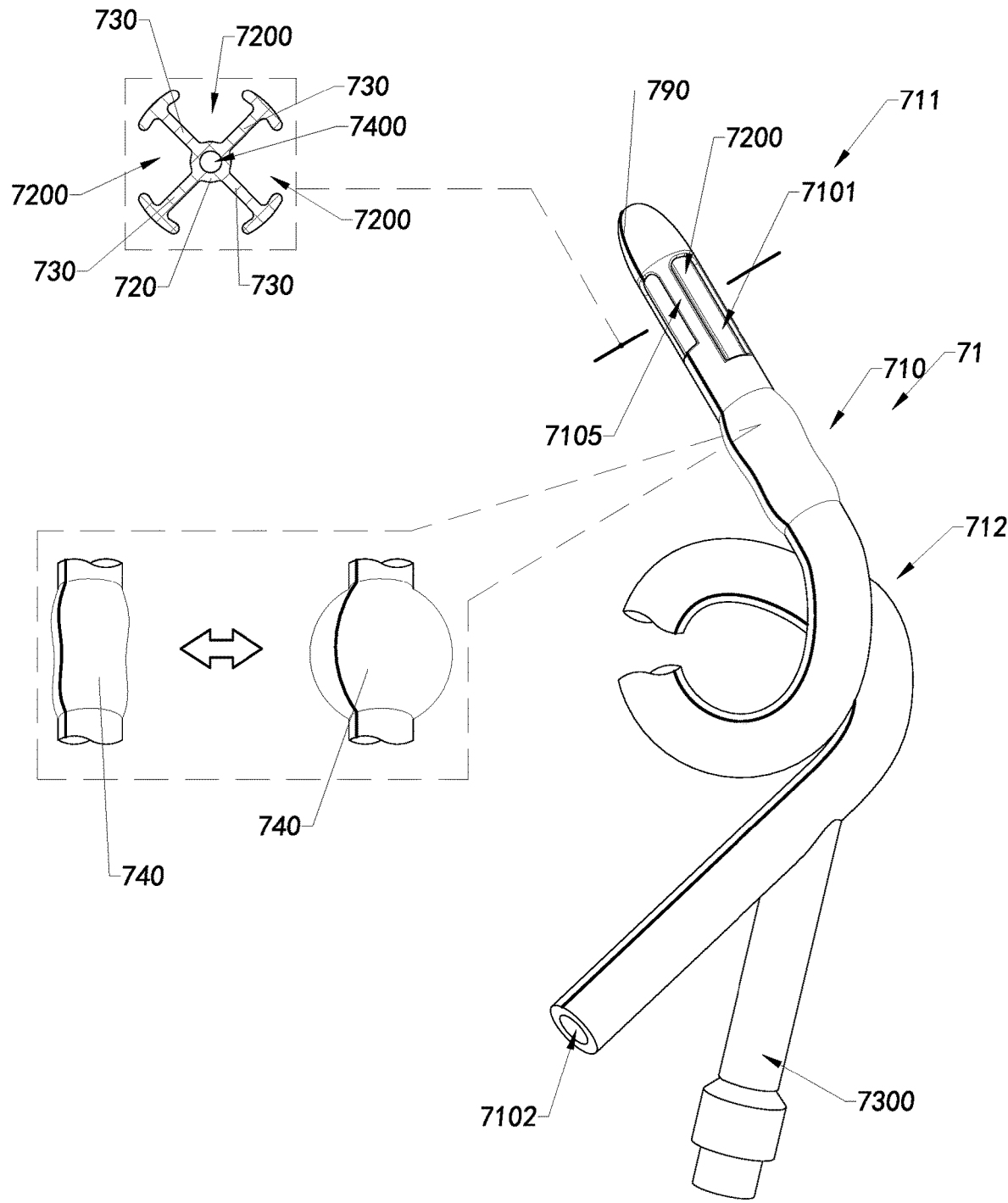
FIG. 2A is a schematic view of a nephrostomy tube according to a preferred embodiment of the present invention.
Figure 2B:
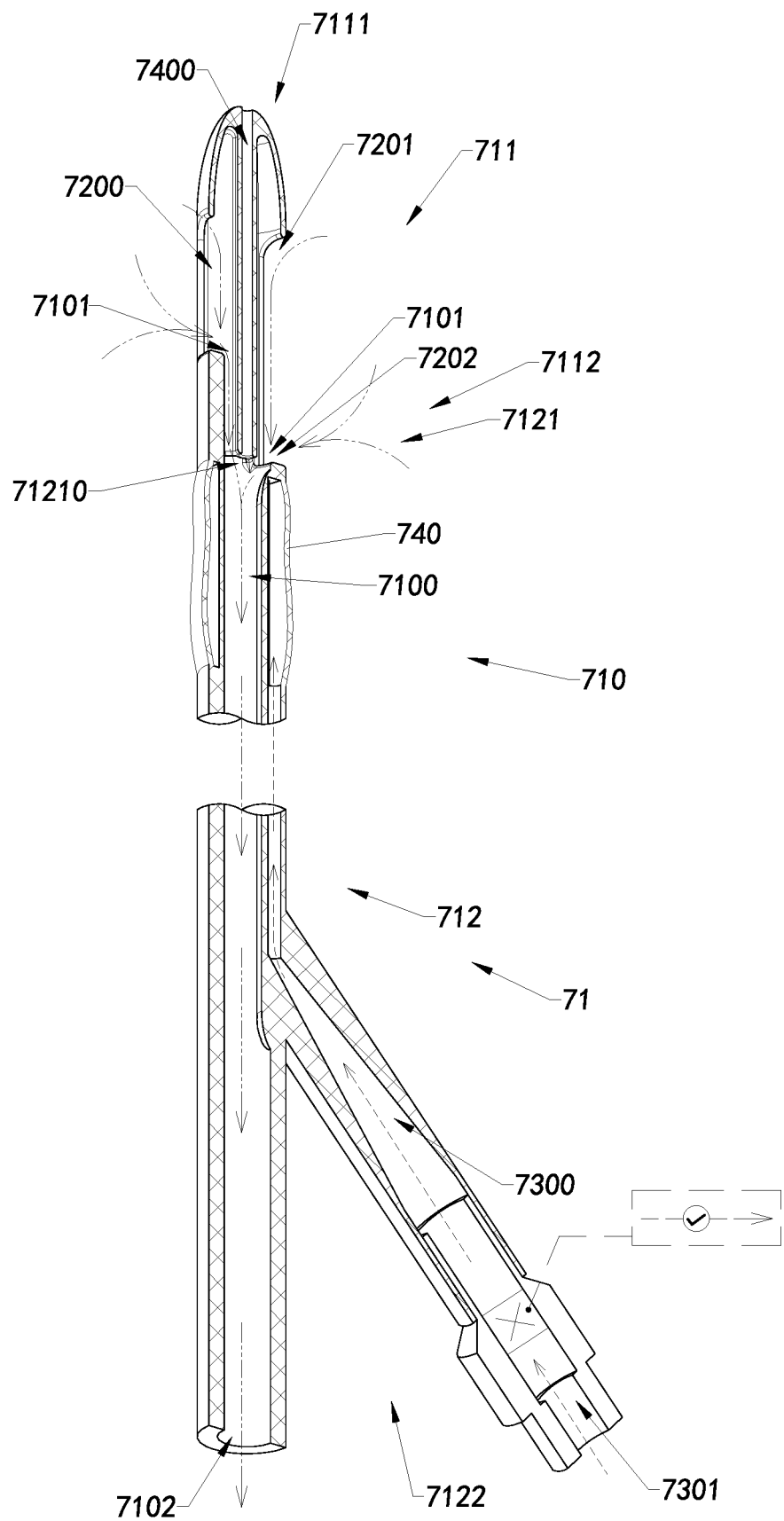
FIG. 2B is a schematic cross-sectional view of the nephrostomy tube according to the preferred embodiment of the present invention.
Figure 3A:
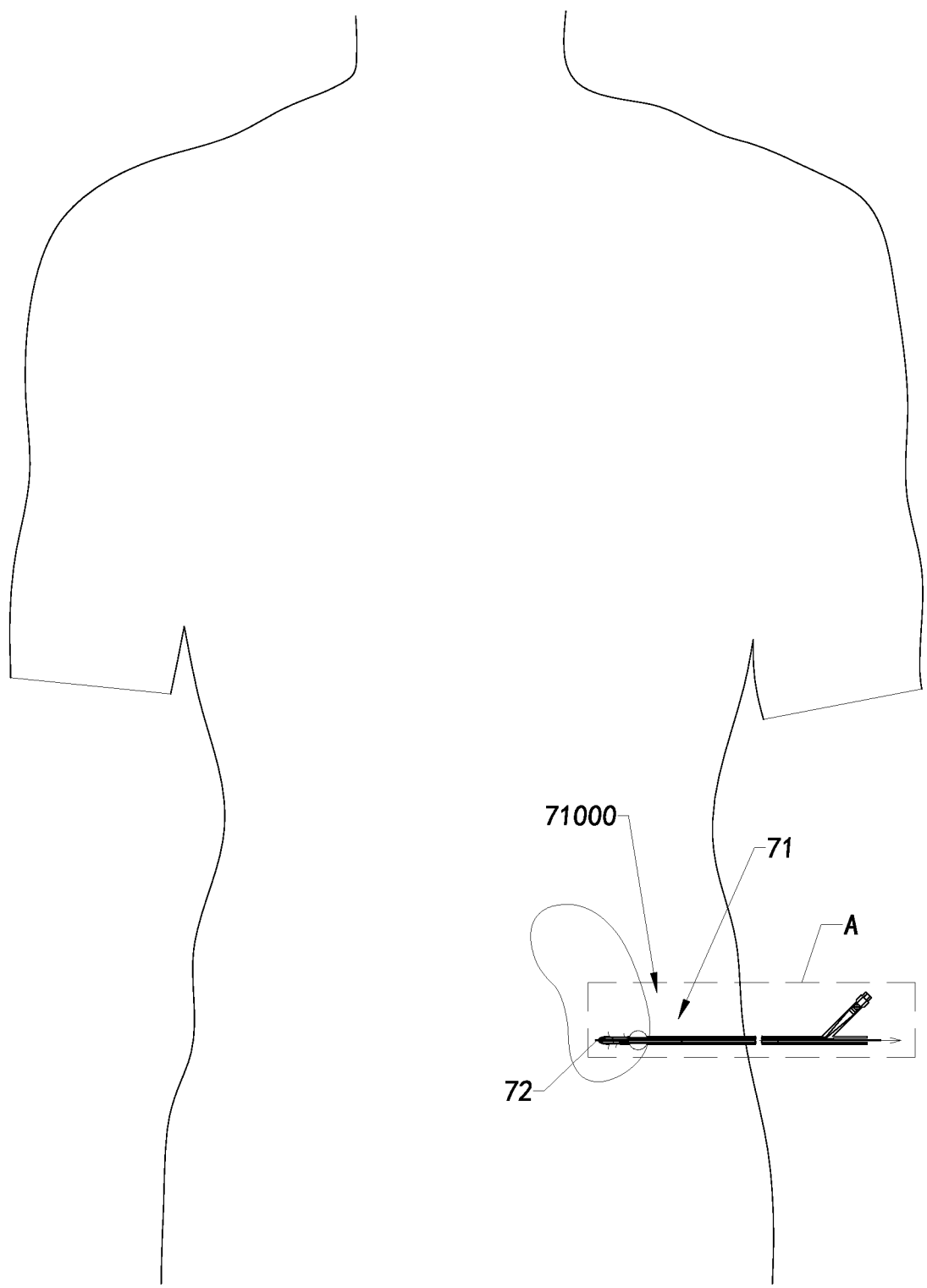
FIGS. 3A and 3B are schematic view of a nephrostomy tube assembly according to a preferred embodiment of the present invention.
Figure 3B:
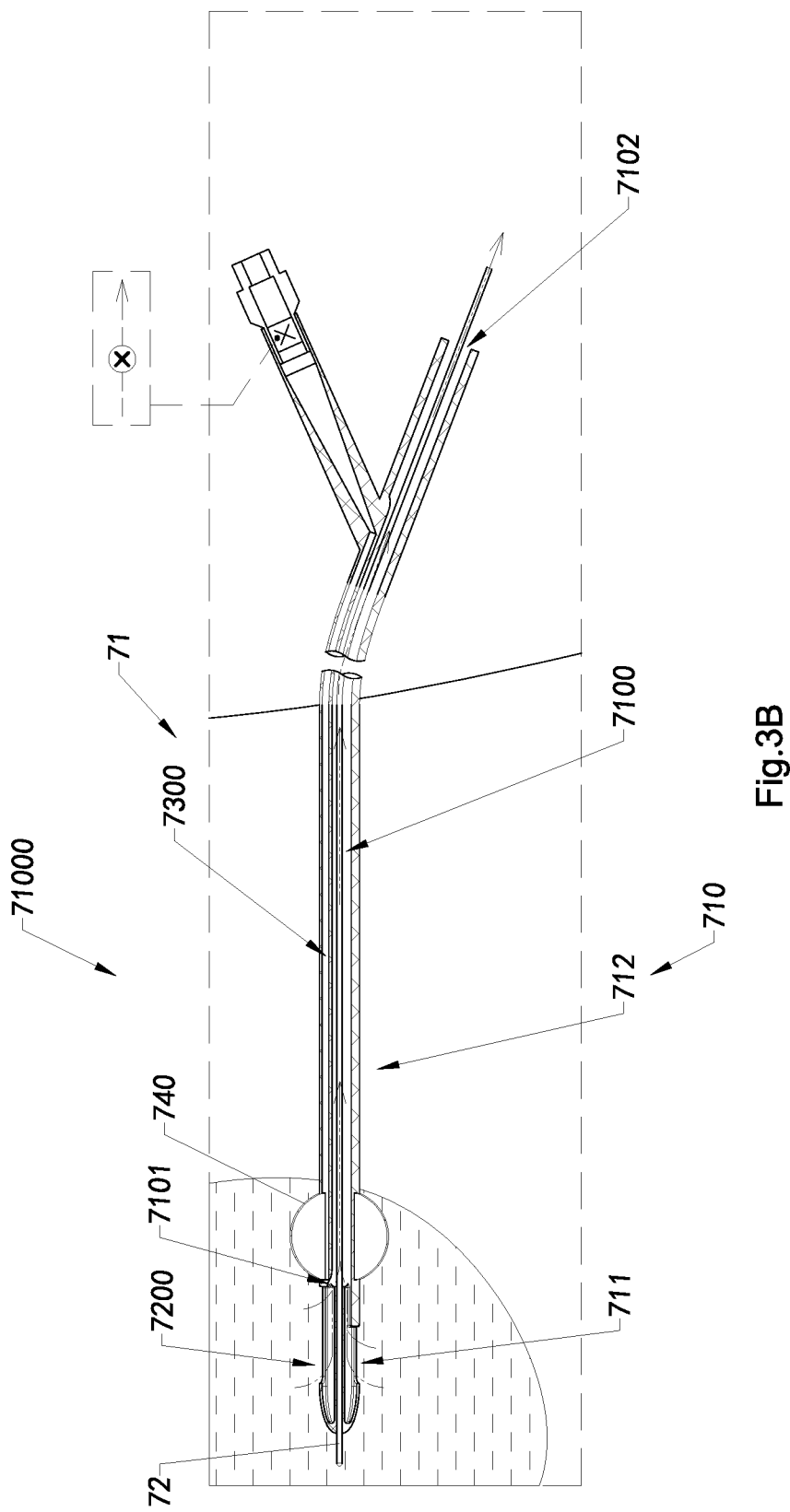

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIGS. 2A to 3B of the drawings, a nephrostomy tube 71 and a nephrostomy tube assembly 71000 is illustrated according to a preferred embodiment of the present invention.

The nephrostomy tube assembly 71000 may comprise the nephrostomy tube 71 and at least one mounting member 72, wherein the mounting member 72 is adapted for guiding the nephrostomy tube 71 into the human body. Of course, it is understandable that the nephrostomy tube 71 can also be directly entered the human body in certain application scenarios.

During use, the nephrostomy tube 71 can reduce the risk of being blocked as much as possible, so that the fluids in the body can be smoothly drained out of the body through the nephrostomy tube 71.

More particularly, the nephrostomy tube 71 has at least two drainage inlets 7101, a drainage channel 7100, a drainage outlet 7102, and at least two guiding grooves 7200, wherein the drainage inlets 7101 and the drainage outlet 7102 are communicated with the drainage channel 7100 respectively. The fluid in the human body is adapted to enter into the drainage channel 7100 through the drainage inlets 7101, and then to leave the human body through the drainage outlet 7102. It is worth mentioning that the form of the fluid is not specifically limited in this disclosure, for instance, the fluid may be a liquid, a liquid-solid mixture, etc.

The guiding grooves 7200 are communicated with the drainage inlets 7101 for guiding fluid in the human body to the position where the drainage inlets 7101 are located, and then the fluid enters the drainage channel 7100 through the drainage inlets 7101.

Each of the guiding grooves 7200 has a predetermined length, which is designed according to specific needs based on the overall size of the nephrostomy tube, for example, the guiding groove 7200 may have a length of 1 cm~5 cm.

The nephrostomy tube 71 comprises a tubular main body 710, having a front end 7103 and a rear end 7104, wherein the front end 7103 and the rear end 7104 are two ends of the tubular main body 710 respectively. In other words, the front end 7103 and the rear end 7104 are defined at the two ends of the tubular main body 710 respectively. The drainage inlets 7101 and the drainage outlet 7102 are formed at the tubular main body 710, wherein the drainage outlet 7102 is formed at the rear end 7104 of the tubular main body 710.

Furthermore, tubular main body 710 includes a front section 711 and a rear section 712 coupled with the front section 711, wherein the drainage outlet 7102 is located at the rear section 712 of the tubular main body 710, the drainage channel 7100 is located at the rear section 712 of the tubular main body 710, and the guiding groove 7200 is located at the front section 711 of the tubular main body 710. During use, the front section 711 of the tubular main body 710 is adapted to extend into the human body, while the guiding grooves 7200 located at the front section 711 are adapted to guide fluid in the body outward to the drainage inlets 7101, such that the fluid can be drained outward through the drainage channel 7100.

More specifically, the front section 711 has a front-section head end 7111 and a front-section tail end 7112, wherein the front-section head end 7111 forms the front end 7103 of the front-section head end 7111. The rear section 712 has a rear-section front end 7121 and a rear-section tail end 7122, wherein the tube rear end 7122 forms the rear end 7104 of the tubular main body 710, and the front-section tail end 7112 of the front section 711 is coupled with the rear-section tail end 7122 of the rear section 712.

In this disclosure, the guiding grooves 7200 are extended between the front-section head end 7111 and the front-section tail end 7112 of the front section 711. Specifically, the guiding grooves 7200 may extend from the front-section tail end 7112 directly towards the front-section head end 7111 of the front section 711. Alternatively, the guiding grooves 7200 may be extended from the front-section head end 7111 directly towards the front-section tail end 7112 of the front section 711. Or, both ends of each of the guiding grooves 7200 are not in contact with the front-section head end 7111 and the front-section tail end 7112 of the front section 711. In other words, the ends of each of the guiding grooves 7200 may be located at the front-section head end 7111 of the front section 711, or may be located at the front-section tail end 7112 of the front section 711, or may be located at between the front-section head end 7111 and the front-section tail end 7112 of the front section 711.

Furthermore, the tubular main body 710 has an outer surface 7105, and a part of the outer surface 7105 at the front section 711 of the tubular main body 710 is indented inward to form the guiding grooves 7200, wherein the guiding grooves 7200 are communicated with the external. In addition, the guiding grooves 7200 are extended along a length direction defined by the tubular main body 710 for guiding the fluid towards the drainage inlets 7101.

It is worth mentioning that it is not necessary that one drainage inlet 7101 corresponds to one guiding groove 7200 respectively. In certain examples, one drainage inlet 7101 may corresponds to two or more guiding grooves 7200, while one guiding groove 7200 may corresponds to two or more drainage inlets 7101.

In one embodiment of the present invention, there are four drainage inlets 7101 and four guiding grooves 7200. It is understandable that the number of the drainage inlets 7101 can be two, three, five, six or more, and the number of the guiding grooves 7200 can be two, three, five, or six or more. The nephrostomy tube 71 further comprises a pillar member 720 and at least two supporting walls 730, wherein the pillar member 720 and the supporting walls 730 format least part of the front section 711. The supporting walls 730 are extended outwardly from the pillar member 720, wherein each of the guiding grooves 7200 is formed between each the adjacent two supporting walls 730. The cross section of each support wall 730 may be "L" shaped or "T" shaped. It is worth mentioning that the outer surface of the supporting walls 730 may be embodied as curved surfaces so as to reduce the risk of damaging human tissues.

In one embodiment of the present invention, there are four supporting walls which are spaced apart with each other to from the guiding grooves 7200.

Accordingly, in one embodiment of the present invention, the drainage inlets 7101 are communicated with the guiding grooves 7200 in such a manner that the fluid will passes through the guiding grooves 7200 before entering into the drainage inlets 7101. And if the fluid contains larger unwanted matters, the larger unwanted matters may be divided into smaller parts by the supporting walls 730 forming the guiding grooves 7200 before entering the drainage inlets 7101, thereby preventing blockage at the drainage inlets 7101. In addition, if one of the drainage inlets 7101 is actually blocked by a larger unwanted matter, since there is a plurality of the drainage inlets 7101, and the adjacent drainage inlets 7101 are separated by the supporting wall 730, the other drainage inlets 7101 can still maintain normal function, ensuring the entire nephrostomy tube 71 still perform normally.

Furthermore, in one embodiment of the present invention, the drainage inlets 7101 are formed at the end portions of the guiding grooves 7200 in its length direction, such that the fluid guided by the guiding grooves 7200 may flow into the drainage inlets 7101 while maintaining its original flow direction. If the fluid contains relatively large unwanted matter, the unwanted matter may be separated by the supporting walls 730 when flowing along the guiding grooves 7200, and if the unwanted matter is relatively small, it may passes along the guiding grooves 7200 and then directly flow into the drainage channel 7100 from the drainage inlets 7101. Of course, the fluid may also be directly sucked into the drainage inlets 7101 from the external without passing through the guiding grooves 7200.

More specifically, in one embodiment of the present invention, the rear section 712 has an opening 71210 formed at the rear-section front end 7121 thereof, wherein the periphery of a surrounding wall of the rear section 712 that forms the opening 71210 may be non-planar or planar. The pillar member 720 and the supporting walls 730 divide the opening 71210 into the plurality of the drainage inlets 7101 at the rear-section front end 7121, thereby reducing the possibility of the opening of being completely blocked. In this embodiment, one end of each of the supporting walls 730 is connected to the pillar member 720, while the other opposed end of the corresponding supporting wall is extended to the inner wall of the rear section 712. It is worth mentioning that the plurality of drainage inlets 7101 may be arranged at the same height, or may be arranged at different heights. In one embodiment of the present invention, at least one of the drainage inlets 7101 is arranged at a position where the opening 71210 of the rear-section front end 7121 is located, and at least another drainage inlet 7101 is arranged at a position above the opening 71210 of the rear-section front end 7121, in such a manner that when the unwanted matter runs into the at least another drainage inlet 7101, it will continue to pass a narrow distance to reach the opening 71210 of the rear-section front end 7121 before entering the drainage channel 7100 with relatively lager inner size.

Figure 10:
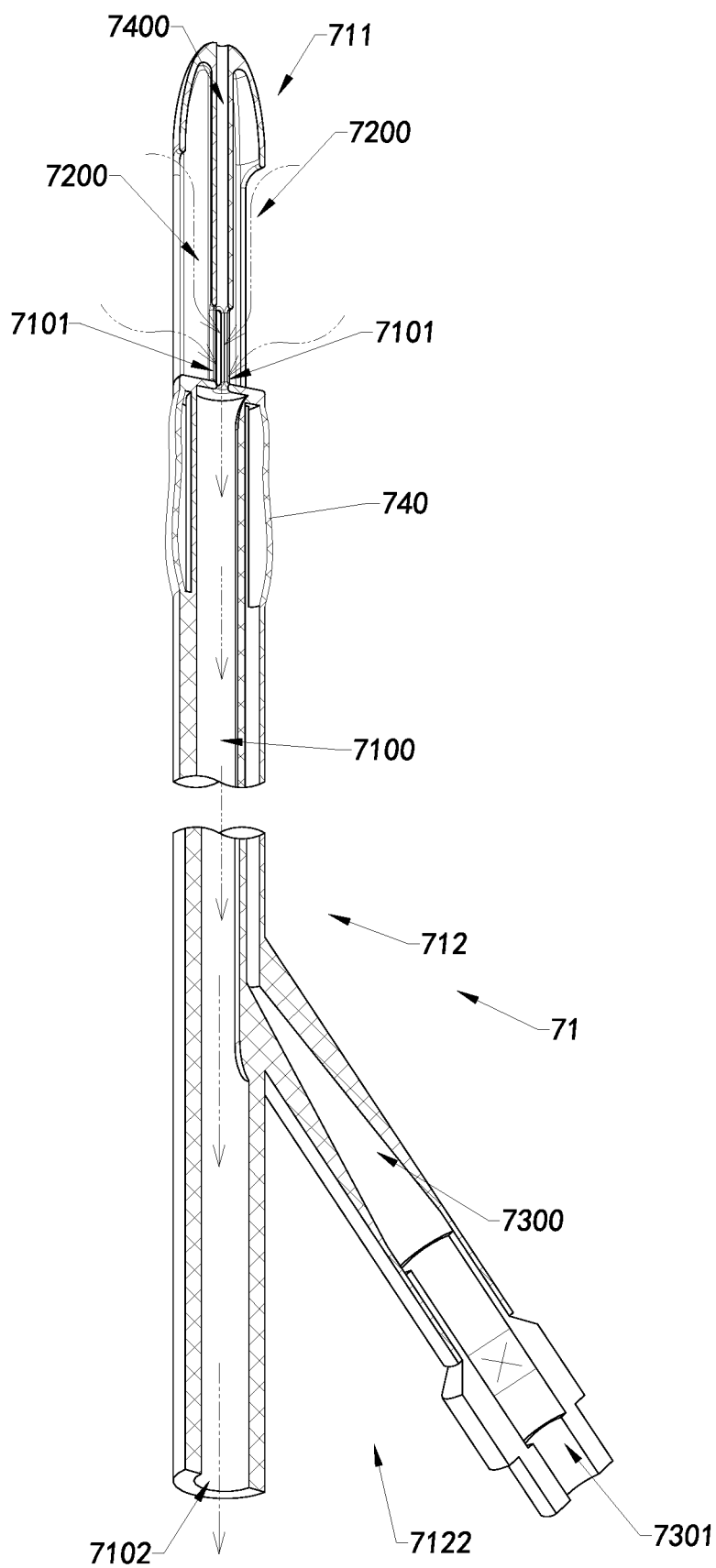
FIG. 10 is schematic view of a nephrostomy tube according to another preferred embodiment of the present invention.

It is worth mentioning that in other embodiments of the present invention, the drainage inlets 7101 may not be provided at the end portions of the guiding grooves 7200, instead, it may be formed at the pillar member 720 or the supporting wall 730, as shown in the FIG. 10 of the drawings, that is, at least one of the drainage inlets is exposed at a preset position of the drainage groove 7200. In other words, the drainage channel 7100 may extend from the drainage inlets 7101 to the rear section 712, or may extend to the front section 711.

Further, each of the guiding grooves 7200 has a drainage starting end 7201 and a drainage ending end 7202, wherein the drainage starting end 7201 is adjacent to the front-section head end 7111 of the front section 711, while, the drainage ending end 7202 is adjacent to the front-section tail end 7112 of the front section 711. In one embodiment, the drainage starting end 7201 may be provided at the front-section head end 7111 of the front section 711. In other embodiments of the present invention, the drainage starting end 7201 may be provided at a position with a predetermined distance from the front-section head end 7111 of the front section 711, such that the outer surface of the front-section head end 7111 of the front section 711 may be embodied as a smooth surface to facilitate the insertion of the nephrostomy tube.

In one embodiment of the present invention, at least one of the guiding grooves 7200 has a distance from the drainage ending end 7202 to the front-section tail end 7112 is greater than that of another guiding groove 7200. Similarly, at least a portion of at least one of the guiding grooves 7200 adjacent to the front-section tail end 7112 is closed, such that for the corresponding guiding groove 7200, the position where the fluid the fluid enters into the drainage channel 7100 from the corresponding guiding groove 7200 is different from other guiding grooves 7200.

More specifically, defining the four guiding grooves 7200 as first guiding groove 7200A, second guiding groove 7200B, third guiding groove 7200C, and fourth guiding groove 7200D, wherein the distance from the drainage ending end 7202 to the front-section tail end 7112 is x, while the drainage ending ends 7202 of the second guiding groove 7200B, the third guiding groove 7200C, and the fourth guiding groove 7200D are located at the front-section tail end 7112 of the front section 711. Accordingly, when an unwanted matter with relatively larger size runs to the drainage ending end 7202 of the first guiding groove 7200A, the guiding grooves 7200 may be blocked by the unwanted matter, while the drainage ending ends 7202 of the second guiding groove 7200B, the third guiding groove 7200C, and the fourth guiding groove 7200D, which are located beside and below the drainage ending end 7202 of the first guiding groove 7200A, are less likely to be blocked at the same time so as to maintain the nephrostomy tube 71 unobstructed as much as possible.

As for the nephrostomy tube 71, when a mass of blood clot moves to the front-section tail end 7112 along the outer wall of the front section 711, at least a portion of the blood clot is adhered to drainage ending end 7202 of the first guiding groove 7200A due to the suction effect at the first guiding groove 7200A, such that the attracted blood clot is unable to move forward to block the drainage ending ends 7202 of the second guiding groove 7200B, the third guiding groove 7200C, and the fourth guiding groove 7200D. In this way, the risk that the nephrostomy tube 71 is being completely blocked causing normal drainage can be significantly reduced. In addition, in one embodiment of the present invention, the front section 711 of the nephrostomy tube 71 is straight in its nature state, and the length of the front section 711 may have a relative small to avoid irritation to tissues within the human body.

Furthermore, the nephrostomy tube 71 further comprises an airbag element 740 and an air channel 7300 communicated with the airbag element 740, wherein the airbag element 740 is coupled with the tubular main body 710 at a position below the drainage inlets 7101, so as not to affect the drainage of the fluid.

In one embodiment of the present invention, the airbag element 740 is provided at the rear section 712 and communicated with the air channel 7300, wherein the air channel 7300 is extended to and connected with a charging port 7301 which is provided at the rear-section tail end 7122 of the rear section 712, such that fluid such as air can be inflated into the airbag element 740 through the air channel 7300 from the charging port 7301.

Furthermore, the nephrostomy tube 71 has an installation channel 7400 communicated with the drainage outlet 7102, wherein the installation channel 7400 is extended from the rear-section tail end 7122 of the rear section 712 to the front-section head end 7111 of the front section 711. The installation channel 7400 is adapted for a mounting member 72 to pass through, and via the mounting member 72, the nephrostomy tube 71 can be guided to a predetermined position within the human body. In one embodiment of the present, the mounting member 72 is embodied as a guiding wire. More specifically, the portion of the installation channel 7400 at the front-section head end 7111 may be sealed, and when the mounting member 72 is required to be inserted into the nephrostomy tube 71, at least a portion of the front-section head end 7111 may be cut off so as to expose the installation channel 7400, and then the nephrostomy tube 71 can be guided to the predetermined position via the mounting member 72.

In one embodiment of the present invention, the installation channel 7400 shares at least a portion with the drainage channel 7100, for instance, the portion of the air channel 7300 at the rear section 712 is shared by the drainage channel 7100. It is worth mentioning that when there is no mounting member 72 installed in the installation channel 7400, the installation channel 7400 can also serve as a drainage channel.

Furthermore, the nephrostomy tube 71 further comprises a marking line 790 provided at the tubular main body 710, such that the positions of the tubular main body 710 can be recognized via the marking line 790 when the tubular main body 710 is inserted into the human body. In one embodiment, at least a portion of the marking line 790 is concealedly embedded in the tubular main body 710, and the concealed line part is visible under X-ray irradiation. Preferably, the marking line 790 is extended from one end of the tubular main body 710 to the opposed other end thereof. It is worth mentioning that the marking line 790 may not be a continuous line, and it only needs to be visible under X-rays or other specific environments.

Further, a comparative experiment is performed on the existing nephrostomy tube A and the nephrostomy tube B in this present invention, wherein the diameters of the two nephrostomy tubes are the same.

The experiment comprises the following steps.

① dispose the conventional nephrostomy tube A and the nephrostomy tube B into a mineral water bottle with a capacity of 350 ml, and then adjust the relative posture between the mineral water bottle and the conventional nephrostomy tube A and the relative posture between the mineral water bottle and the nephrostomy tube B to a position that most of the fluid stored in the mineral water bottle can be drained outside from the mineral water bottle through the conventional nephrostomy tube A and the nephrostomy tube B.

As it turns out that the conventional nephrostomy tube A takes 34 seconds to complete the drainage, while the drainage time of the nephrostomy tube B of the present invention is 35 seconds.

② The only difference from the first step is that in the second step, the fluid in the mineral water bottle is replaced with a mixed fluid of 50 ml blood and 50 ml normal saline, and the drainage experiment starts until blood clot is formed in the mixed fluid after letting the mineral water bottle stand for 15 minutes.

Figure 11:
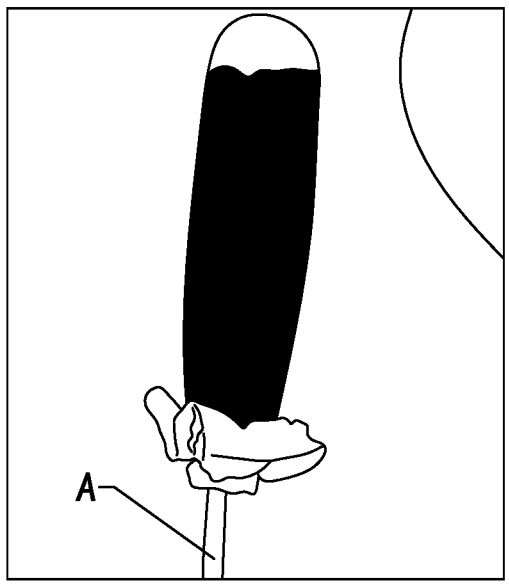
FIG. 11 is an experimental comparison diagram of the nephrostomy tube and the conventional nephrostomy tube according to a preferred embodiment of the present invention.
Figure 11:
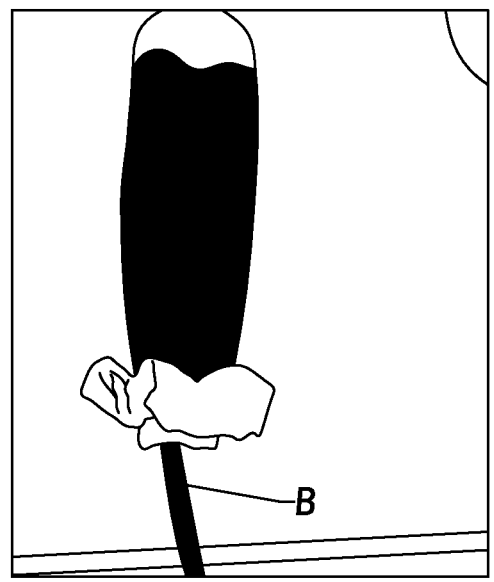
Figure 12:
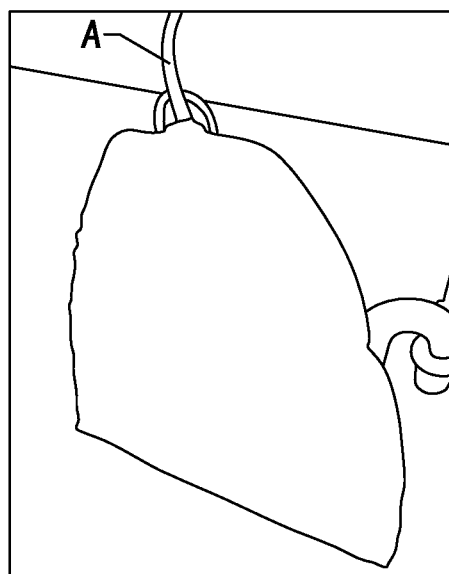
FIG. 12 is a schematic diagram of the experimental result comparison between the nephrostomy tube and the conventional nephrostomy tube according to the above preferred embodiment of the present invention.
Figure 12:
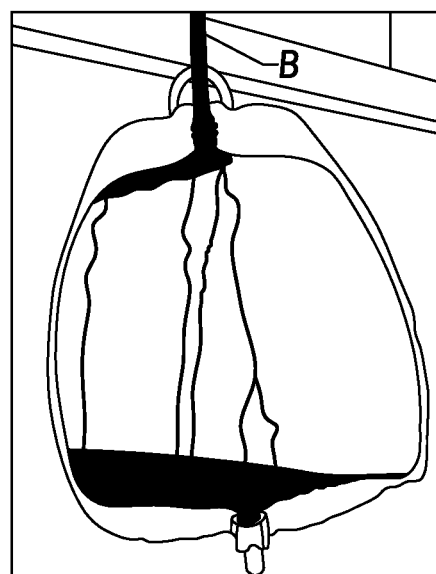

Referring to the FIGS. 11 and 12 of the drawings, as it turns out that the existing nephrostomy tube A cannot complete the drainage, and it is blocked by blood clots, while the nephrostomy tube B of the present invention is capable of completing the drainage in 738 seconds.

③ Different from the first and the second steps, the fluid in the third is replaced with a mixed fluid of 20 ml blood and 80 ml normal saline, and the drainage test is began blood clot is formed in the mixed fluid after letting the mineral water bottle stand for 15 minutes.

As it turns out, it takes the conventional nephrostomy tube A 10 minutes to finish the drainage, and the flow rate is relatively small in a period of the drainage time, while the nephrostomy tube B only takes 28 seconds to complete the drainage.

The conclusion is that compared with the conventional nephrostomy tube A, the nephrostomy tube is less likely to encounter blockage.

Figure 4:
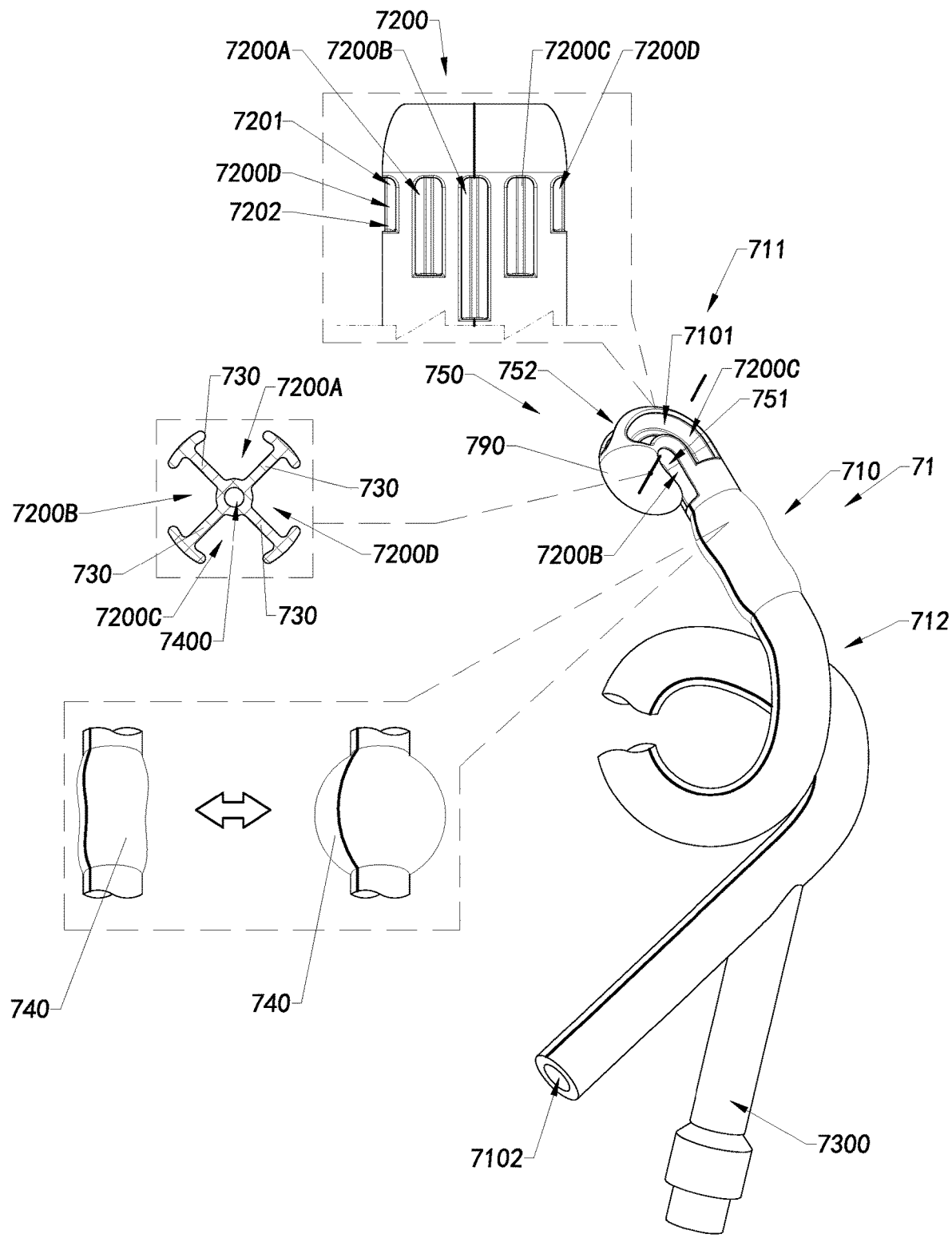
FIG. 4 is schematic view of a nephrostomy tube according to another preferred embodiment of the present invention.
Figure 5:
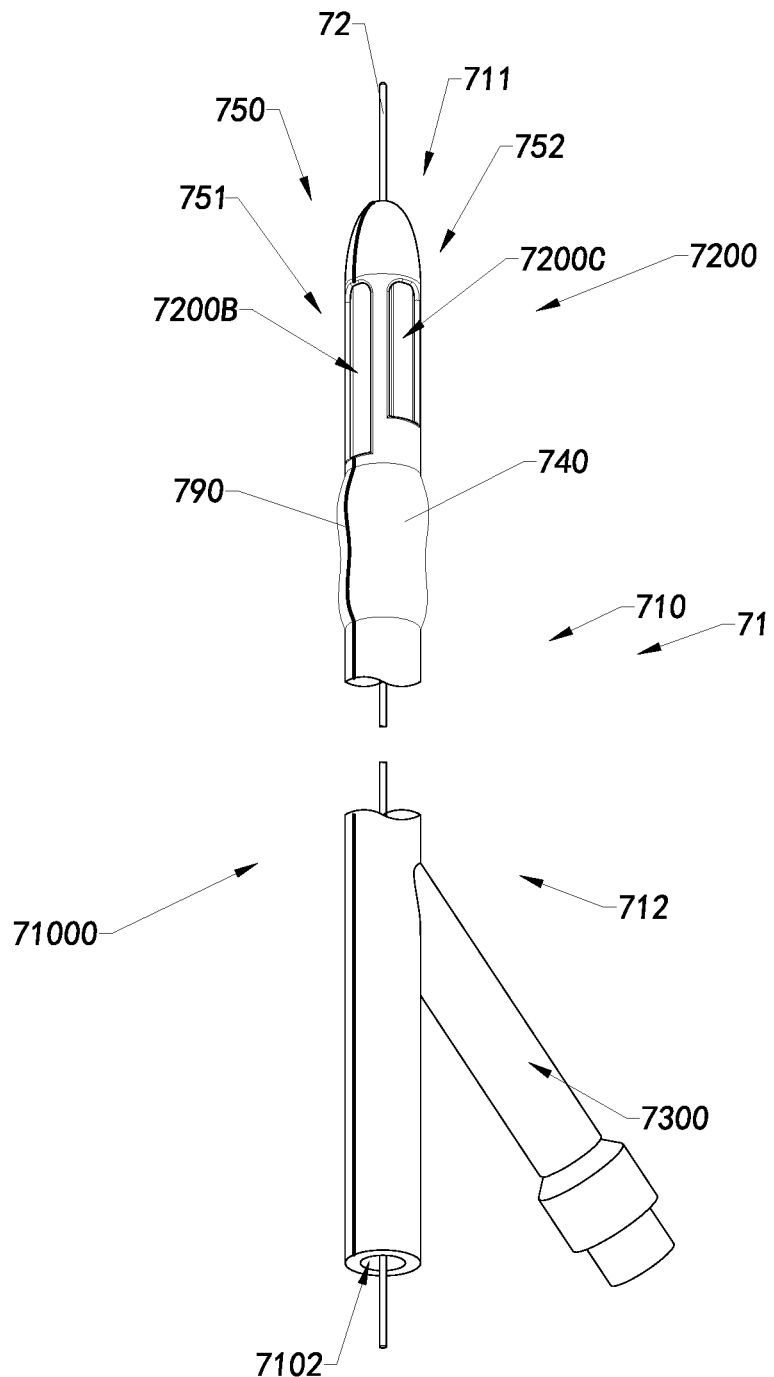
FIG. 5 is schematic view of a nephrostomy tube assembly according to another preferred embodiment of the present invention.

Referring to the FIGS. 4 and 5 of the drawings, another preferred embodiment of the nephrostomy tube 71 and the nephrostomy tube assembly 71000 are illustrated.

The main difference between this preferred embodiment and the above embodiment is in the tubular main body 710 of the nephrostomy tube 71.

Accordingly, in this preferred embodiment, the tubular main body 710 further includes a bending portion 750. More specifically, the front section 711 of the tubular main body 710 is bent from the front-section head end 7111 to form the bending portion 750, in order to reduce the irritation to the human or animal body caused by the nephrostomy tube 71 after being disposed within the body.

The front section 711 of the tubular main body 710 of the nephrostomy tube 71 is bent around the front-section head end 7111 to form the bending portion 750, while the guiding grooves 7200 is bent along with the front section 711 to change the flow path of the fluid into a curved path.

During the bending process, the supporting walls 730 and the pillar member 720, which form the guiding grooves 7200, are bent at the same time to facilitate the separation of larger blood clots into smaller blood clots.

Furthermore, there are four guiding grooves 7200 provided in this preferred embodiment. The bending portion 750 has a bending front side 751 and a bending back side bending back side 752 opposed with the bending front side 751, wherein the bending front side 751 is the side that the front section 711 is bent towards.

The four guiding grooves 7200 are the first guiding groove 7200A, the second guiding groove 7200B, the third guiding groove 7200C, and the fourth guiding groove 7200D, wherein the first guiding groove 7200A, the second guiding groove 7200B, the third guiding groove 7200C, and the fourth guiding groove 7200D are circumferentially arranged around the pillar member 720 of the front section 711. The second guiding groove 7200B is provided at the bending back side 752 of the bending portion 750, the fourth guiding groove 7200D is provided at the bending front side 751 of the bending portion 750, while the first guiding groove 7200A and the third guiding groove 7200C are arranged oppositely and located between the pillar member second guiding groove 7200B and the fourth guiding groove 7200D.

Furthermore, the drainage ending ends 7202 of the first guiding groove 7200A, the second guiding groove 7200B, the third guiding groove 7200C, and the fourth guiding groove 7200D are configured in step-shaped. More specifically, compared with the first guiding groove 7200A, the third guiding groove 7200C, and the fourth guiding groove 7200D, the drainage ending end 7202 of the second guiding groove 7200B is closer to the drainage outlet 7102, while compared with the fourth guiding groove 7200D, the drainage ending ends 7202 of the first guiding groove 7200A and the third guiding groove 7200C are closer to the drainage outlet 7102. In other words, the drainage ending end 7202 of the guiding grooves 7200, which is located at the bending front side 751 of the bending portion 750, is farthest from the drainage outlet 7102.

Taking a point below the guiding grooves 7200 as a reference point, the distance between the drainage ending end 7202 of the second guiding groove 7200B and the reference point is L1, the distances between the drainage ending ends 7202 of the first guiding groove 7200A and the third guiding groove 7200C and the reference point are L2, and the distance between the drainage ending end 7202 of the fourth guiding groove 7200D and the reference point is L3, wherein the L1 is less than L2 while L2 is less than L3. In addition, the length of the second guiding groove 7200B is greater than those of the first guiding groove 7200A, third guiding groove 7200C and the fourth guiding groove 7200D, while the drainage starting ends 7201 of the first guiding groove 7200A, the second guiding groove 7200B, the third guiding groove 7200C and the fourth guiding groove 7200D are arranged in coplanar. When the nephrostomy tube 71 is disposed in human body with the front section 711 naturally bent to from the bending portion 750, the second guiding groove 7200B is exposed to the external while most of the fourth guiding groove 7200D is hidden inside the body. The first guiding groove 7200A and the third guiding groove 7200C are located between the second guiding groove 7200B and the fourth guiding groove 7200D respectively for playing a drainage role. In the four guiding grooves 7200, the second guiding groove 7200B plays the main drainage role.

Moreover, the drainage inlets 7101, corresponding with the first guiding groove 7200A, the second guiding groove 7200B, the third guiding groove 7200C, and the fourth guiding groove 7200D, are located at the drainage ending ends 7202 of the guiding grooves 7200. Due to the differential arrangement in height of the drainage ending ends 7202, the drainage inlets 7101 are also arranged deferentially in height, such that it is hard for the unwanted matter to simultaneously block the drainage inlets 7101 at the same time. Always is the case that one of the drainage inlets 7101 is blocked while the other drainage inlets 7101 can still maintain their normal function, thereby enhancing the ability of the nephrostomy tube 71.

It is worth mentioning that the differential arrangement in height of the drainage ending ends 7202 of the first guiding groove 7200A, the second guiding groove 7200B, the third guiding groove 7200C, and the fourth guiding groove 7200D in this preferred embodiment is merely exemplary, which is not intended to be limited in the present invention.

Figure 6:
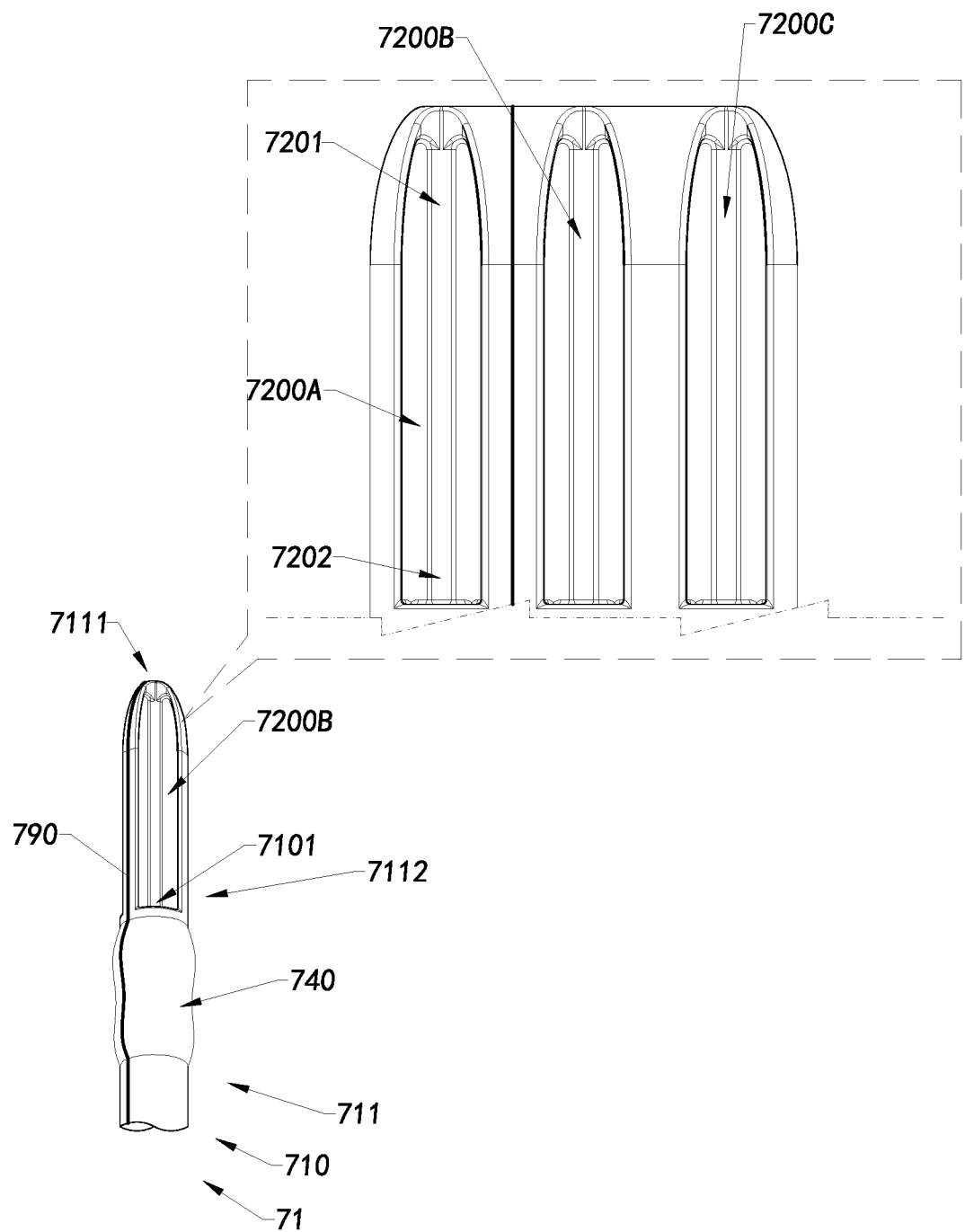
FIG. 6 is partial schematic view of a nephrostomy tube according to another preferred embodiment of the present invention.

Referring to FIG. 6 of the drawings, a nephrostomy tube 71 according to another preferred embodiment of the present invention is illustrated.

In this preferred embodiment, the front-section head end 7111 of the front section 711 is penetrated towards the rear-section tail end 7122 of the rear section 712 such that the space between the front-section head end 7111 and the rear-section tail end 7122 forms a portion of the installation channel 7400.

Viewing from the front-section head end 7111, the installation channel 7400 can be observed. In other words, the installation channel 7400 is exposed at the front-section head end 7111. During use, the nephrostomy tube 71 can be guided into the human body via the mounting member 72 to a predetermined position and the front section 711 of the nephrostomy tube 71 returns to its original state when the mounting member 72 is withdrawn.

During withdrawing the nephrostomy tube 71 out of the human body, the mounting member 72 is inserted into the installation channel 7400, such that the bent front section 711 is deployed along the mounting member 72 to a straight line, and then the nephrostomy tube 71 can be pulled out of the human body without causing excessive irritation to the wound by the bent front section 711.

In addition, the first guiding groove 7200A, the second guiding groove 7200B, and the third guiding groove 7200C may extend to the front-section head end 7111.

Figure 7:
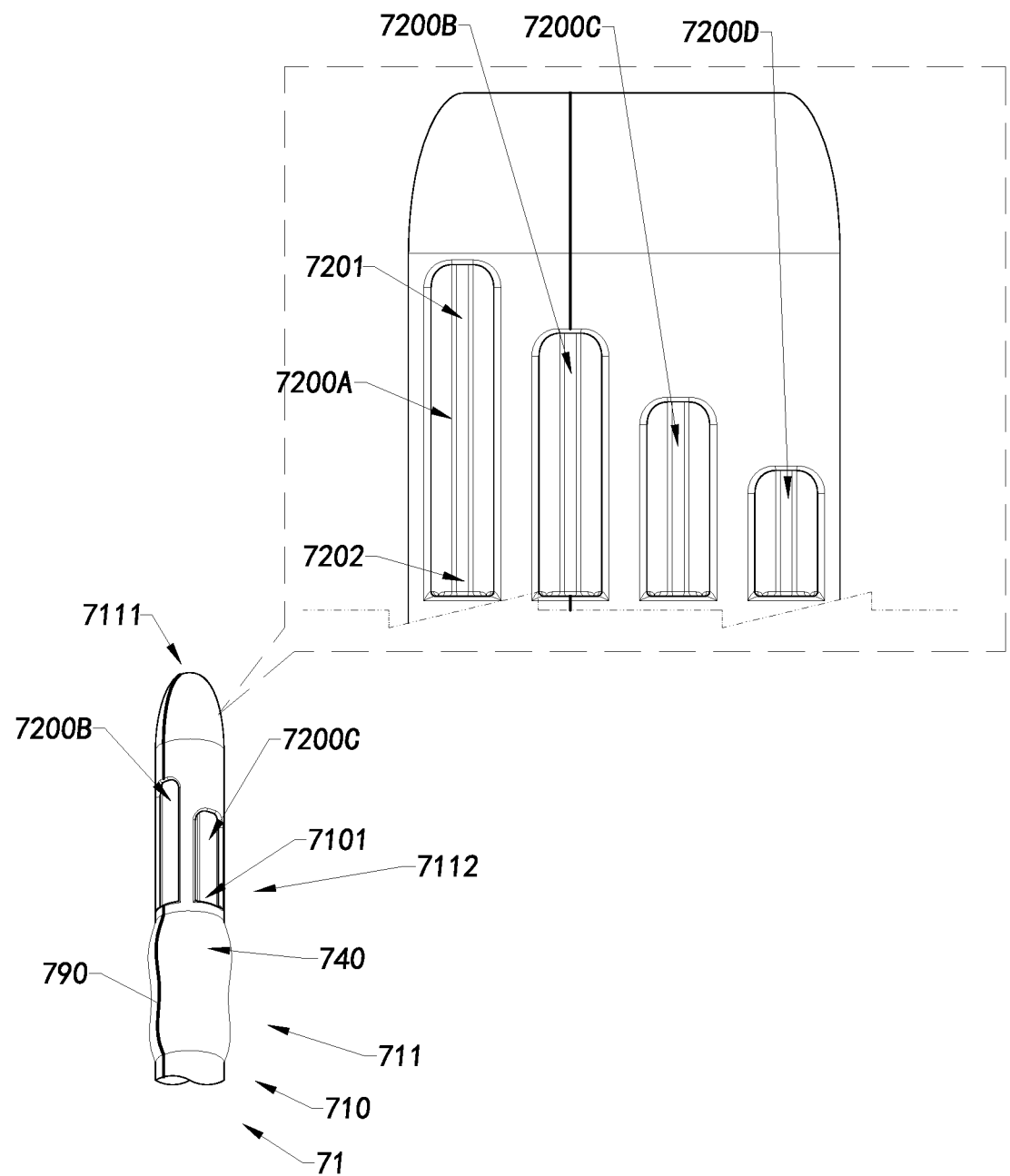
FIG. 7 is partial schematic view of a nephrostomy tube according to another preferred embodiment of the present invention.

Referring to the FIG. 7 of the drawings, a nephrostomy tube 71 according to another preferred embodiment of the present invention is illustrated.

In this preferred embodiment, there are four guiding grooves 7200 provided along the tubular main body 710, which are defined as the first guiding groove 7200A, the second guiding groove 7200B, the third guiding groove 7200C and the fourth guiding groove 7200D. Accordingly, the first guiding groove 7200A, the second guiding groove 7200B, the third guiding groove 7200C and the fourth guiding groove fourth guiding groove 7200D are arranged in sequence along the pillar member 720.

A portion of the front section 711 from a position between the front-section tail end 7112 and the front-section head end 7111 of the front section 711 to the front-section head end 7111 is configured to be naturally bendable to form the bending portion 750. More specifically, at least a portion of the front section 711 is bendable around a center of the front-section head end 7111, just like a pig's tail.

The drainage starting ends 7201 of the first guiding groove 7200A, the second guiding groove 7200B, the third guiding groove 7200C, and the fourth guiding groove 7200D are configured in step-shaped. The distance between the drainage starting end 7201 of the first guiding groove 7200A to the front-section head end 7111 is x, the distance between the drainage starting end 7201 of the second guiding groove 7200B and the front-section head end 7111 is x1, the distance between the drainage starting end 7201 of the third guiding groove 7200C and the front-section head end 7111 is x2 and the distance between the drainage starting end 7201 of the fourth guiding groove 7200D and the front-section head end 7111 is x3, wherein x is less than x1, x1 is less than x2, and x3 is less than x4. The drainage ending ends 7202 of the first guiding groove 7200A, the second guiding groove 7200B, the third guiding groove 7200C, and the fourth guiding groove 7200D are arranged in coplanar.

Since the drainage starting ends 7201 of the first guiding groove 7200A, the second guiding groove 7200B, the third guiding groove 7200C, and the fourth guiding groove 7200D are configured in step-shaped, the probability of the first guiding groove 7200A, the second guiding groove 7200B, the third guiding groove 7200C, and the fourth guiding groove 7200D being blocked at the same time is reduced, so as to keep the nephrostomy tube 71 unblocked as much as possible. In addition, when the bending portion 750 of the tubular main body 710 is formed, the fourth guiding groove 7200D with relatively longer length is located at an outer side of the bending portion 750 in such a manner that the risk of the nephrostomy tube 71 being blocked can be reduced.

Figure 8:
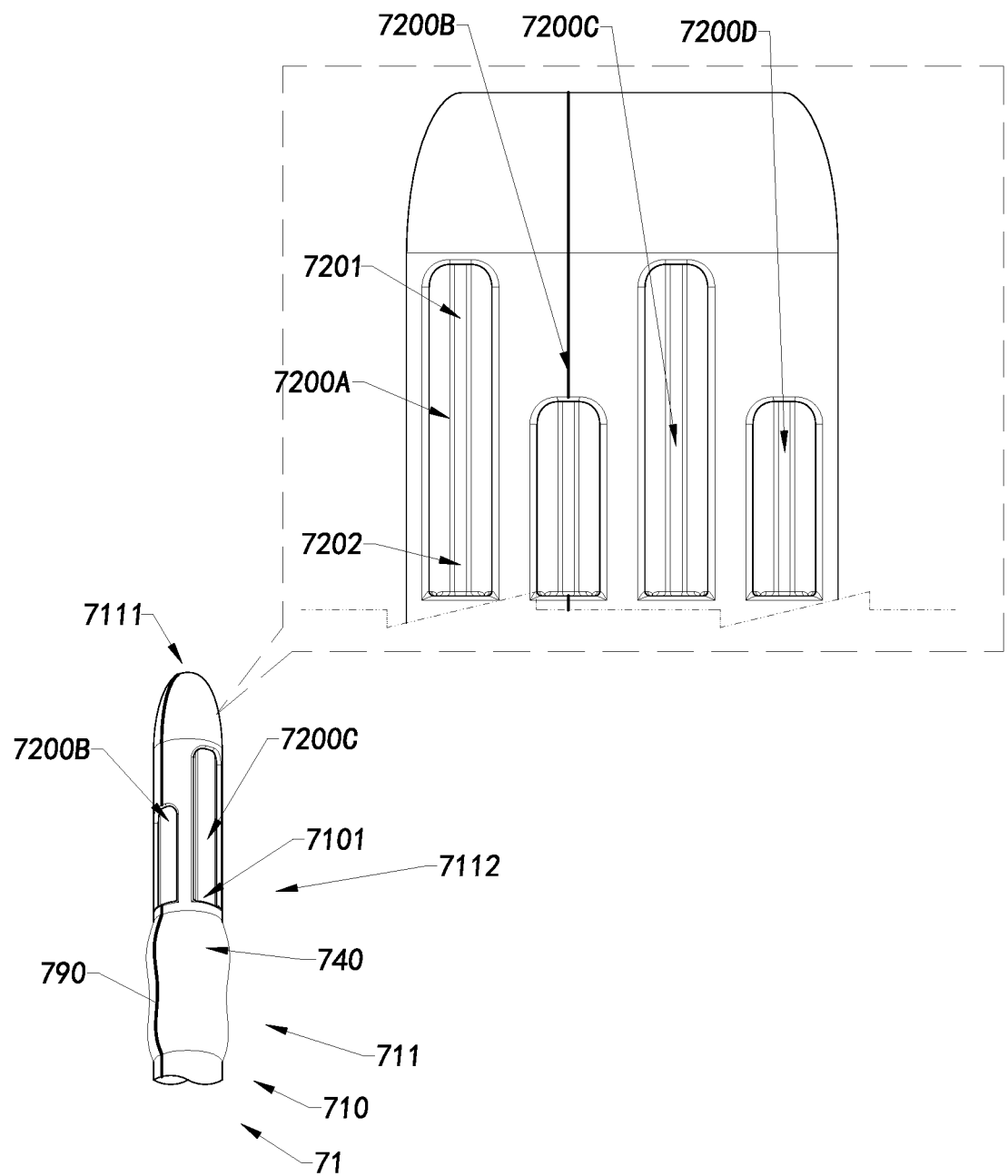
FIG. 8 is partial schematic view of a nephrostomy tube according to another preferred embodiment of the present invention.

Referring to the FIG. 8 of the drawings, a nephrostomy tube 71 according to another preferred embodiment of the present invention is illustrated.

The difference between this preferred embodiment and the above preferred embodiments lies in the arrangement of the guiding grooves 7200. In particular, the guiding grooves 7200 are arranged alternatively in length.

More specifically, there are four guiding grooves 7200 in this preferred embodiment, wherein the four guiding grooves 7200 are provided on the peripheral side of the front section 711, and are arranged alternatively in length.

It is worth mentioning that in this preferred embodiment, each of the four guiding grooves 7200 is corresponding to one drainage inlets 7101. Alternatively, two or more guiding grooves 7200 may correspond to one drainage inlet 7101, while one guiding groove 7200 may correspond to two or more drainage inlets 7101.

Figure 9:
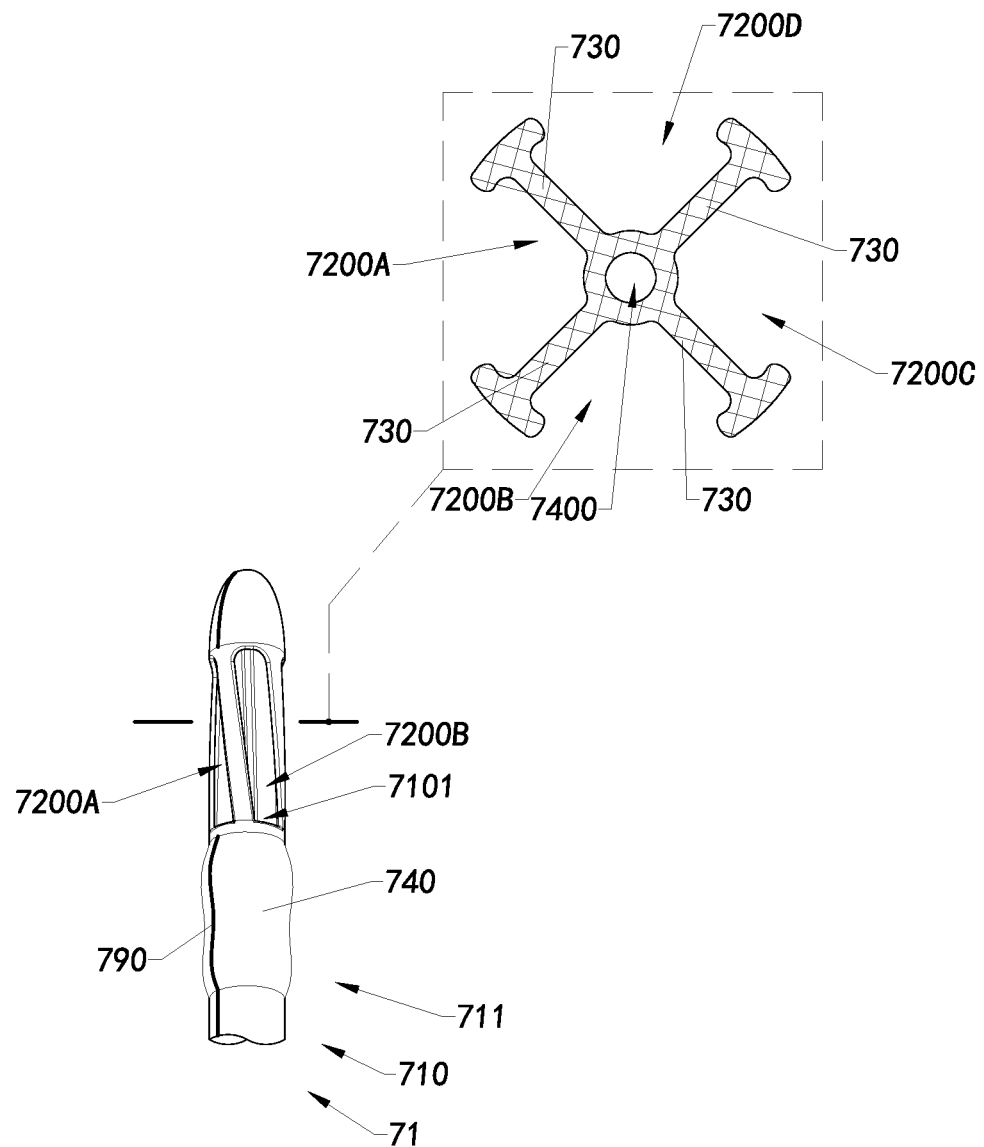
FIG. 9 is partial schematic view of a nephrostomy tube according to another preferred embodiment of the present invention.

Referring to the FIG. 9 of the drawings, a nephrostomy tube 71 according to another preferred embodiment of the present invention is illustrated, wherein the guiding grooves 7200 is located at the front section 711 and curvedly extending between the front-section head end 7111 and the front-section tail end front-section tail end 7112.

The supporting walls 730, which form the guiding grooves 7200, is inclined, such that when blood clot or the like is attached to the guiding grooves 7200 of the nephrostomy tube 71, the blood clot may be separated into smaller pieces by the inclined guiding grooves 7200 in certain cases.

It is worth mentioning that the number of the guiding grooves 7200 may be one, two, three, four or more, and if there is only one guiding groove 7200 provided, the guiding groove 7200 is preferably to spirally extend around the front section 711 in such a manner to increase the travel distance of fluid flowing on the outer surface of the nephrostomy tube 71 while reducing the risk of being blocked.

Figure 13:
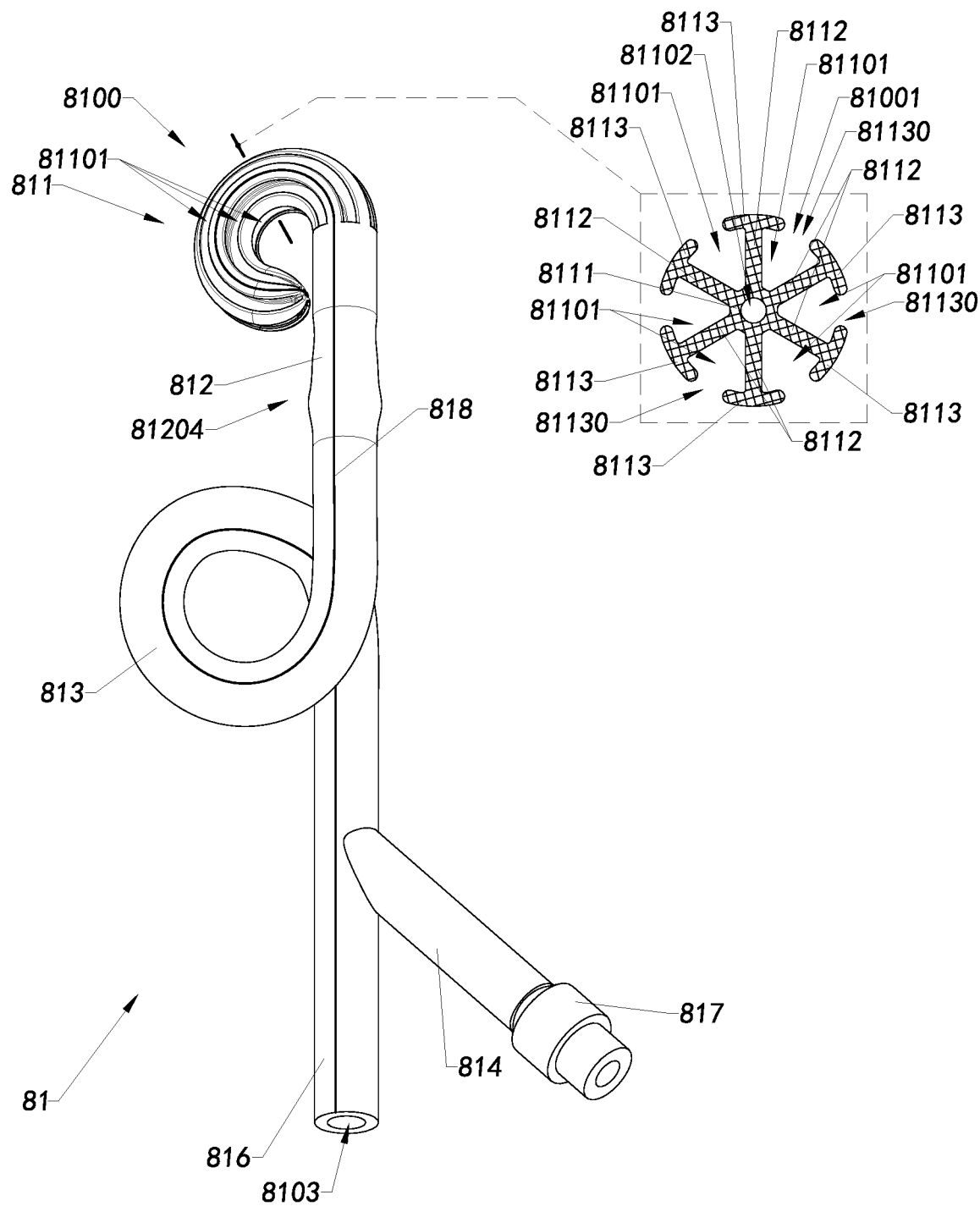
FIG. 13 is a schematic view that illustrates a nephrostomy tube with curved drainage at its bending sate according to a first preferred embodiment of the present invention.
Figure 14:
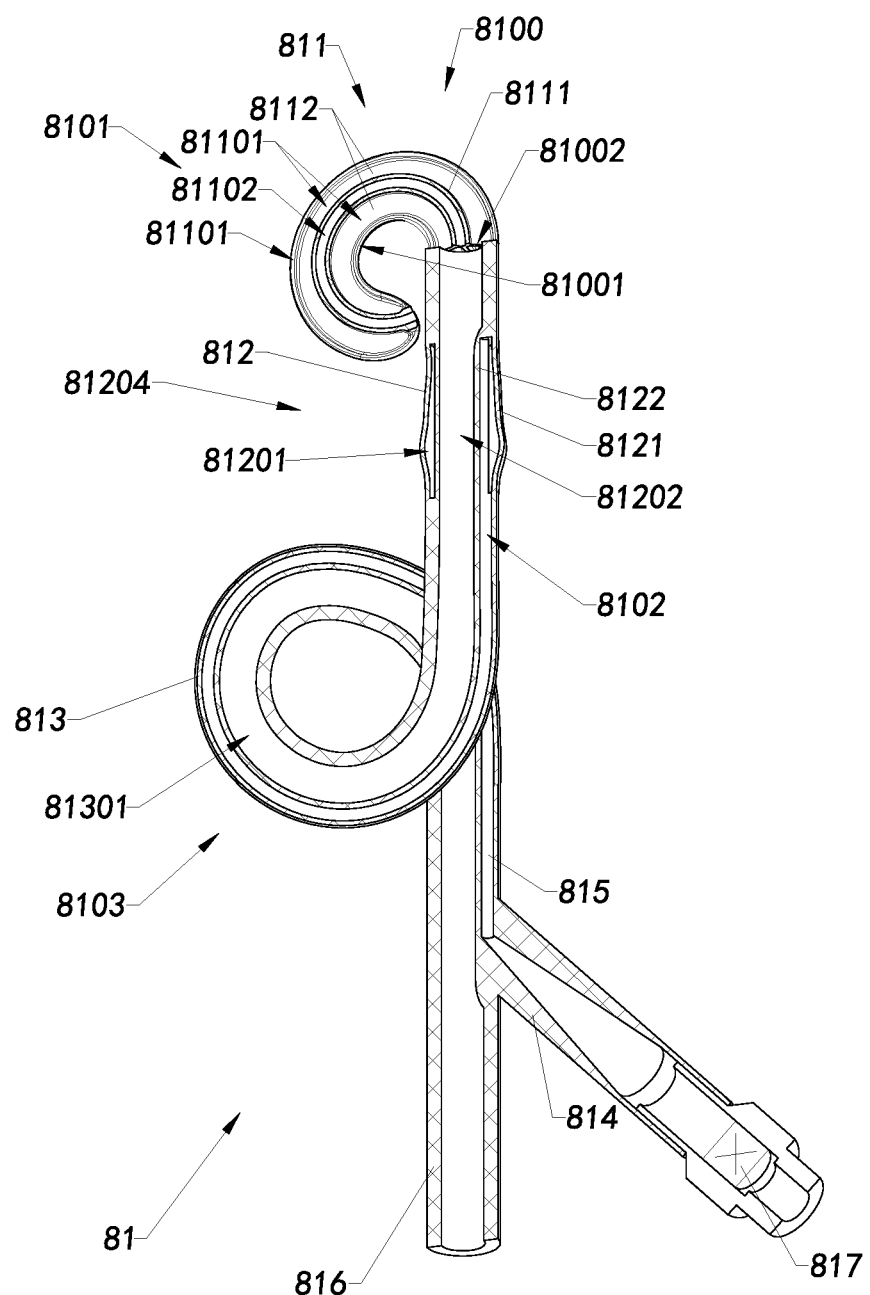
FIG. 14 is a schematic cross-sectional view of the nephrostomy tube with curved drainage shown in the FIG. 13.
Figure 15:
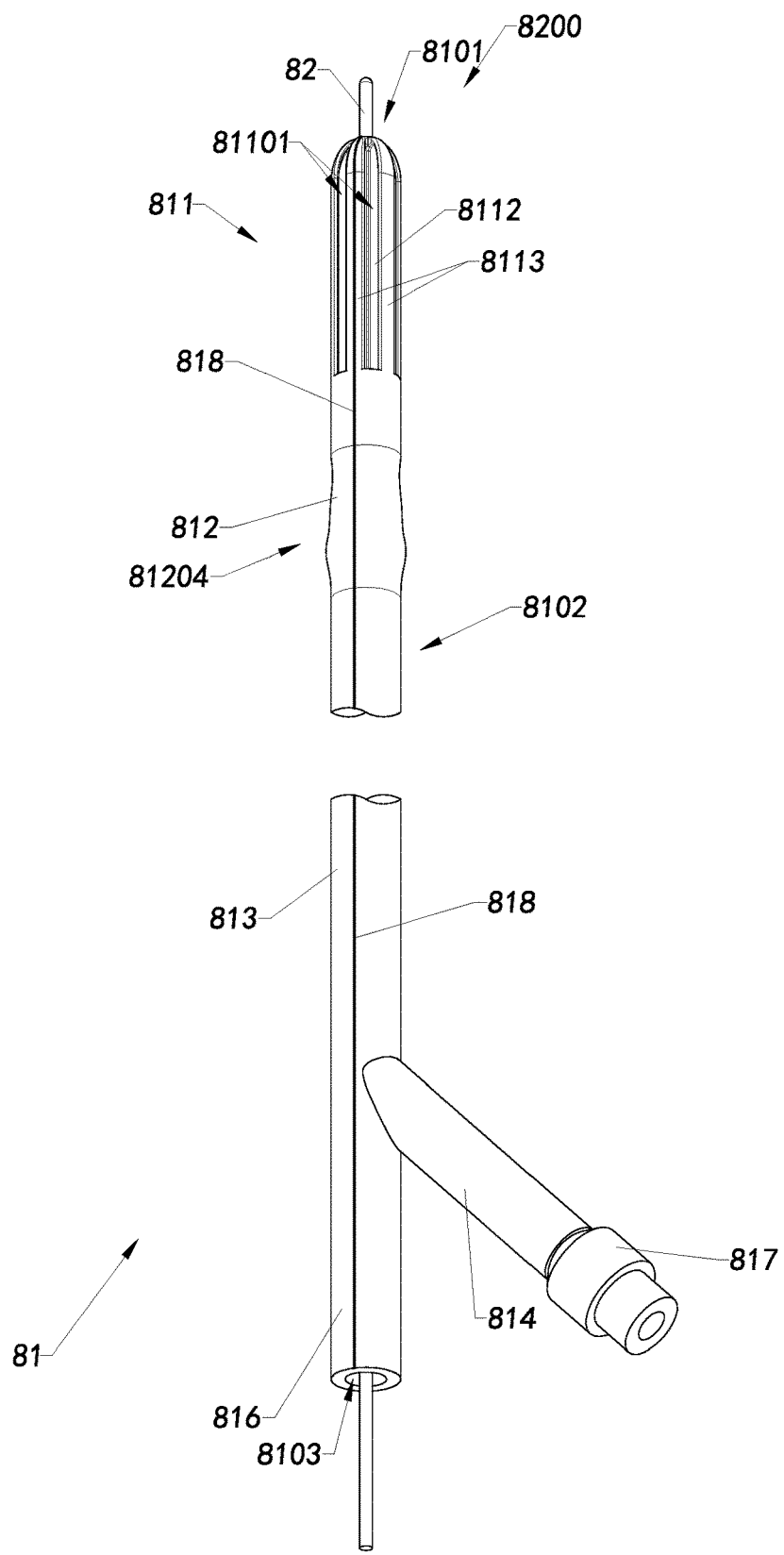
FIG. 15 is a schematic view that illustrates the nephrostomy tube with curved drainage at its stretched sate when being inserted with a guiding member.
Figure 16:
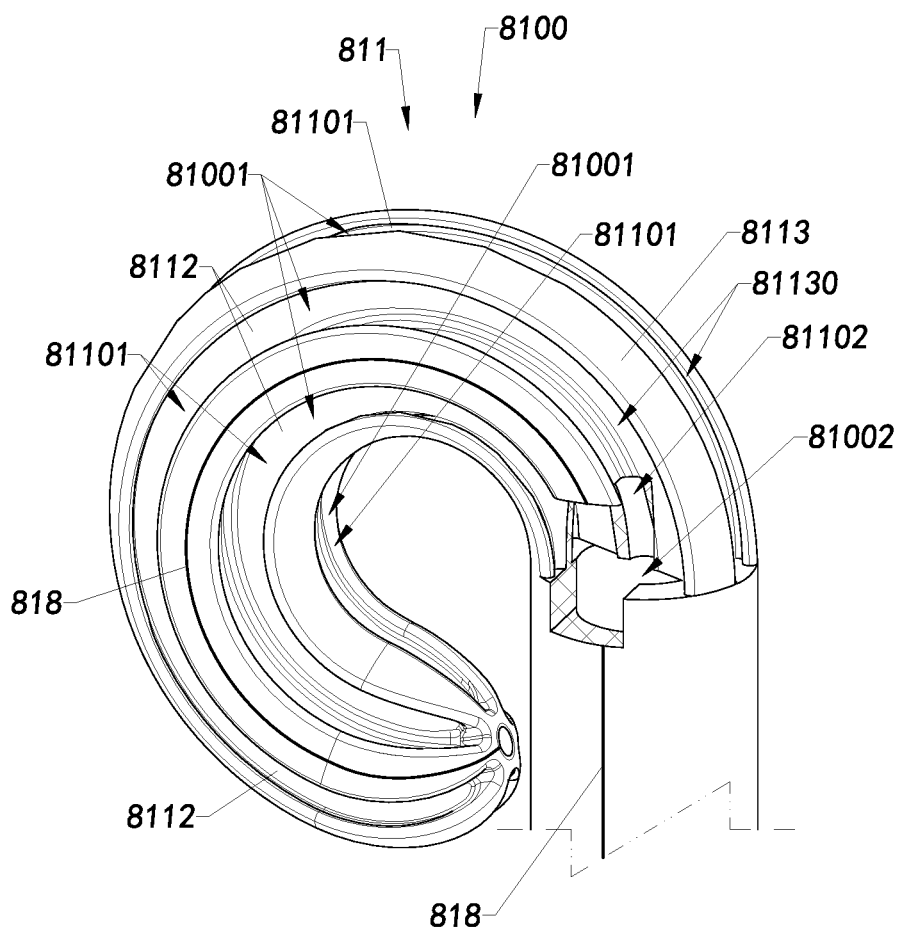
FIG. 16 is a partial enlarged schematic view of the nephrostomy tube with curved drainage according to the first referred embodiment of the present invention, illustrating the structure of the bending head.
Figure 17:
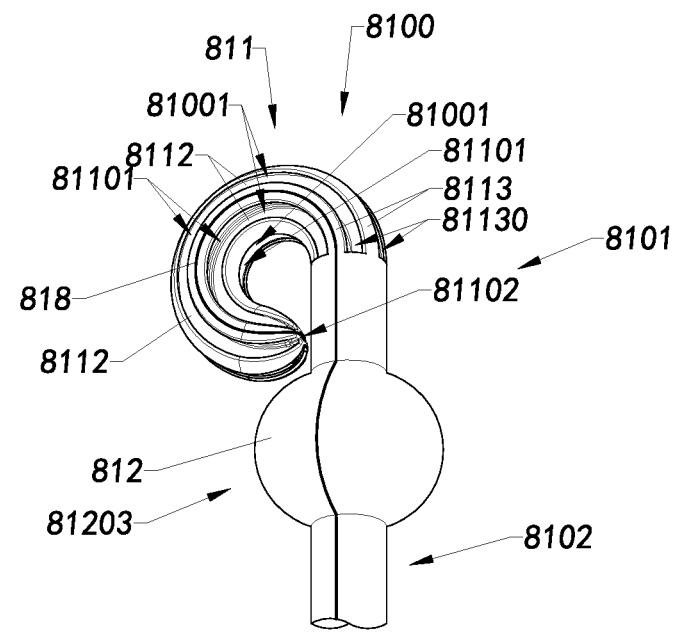
FIG. 17 is a schematic view of the nephrostomy tube with curved drainage at its inflated state.
Figure 17:
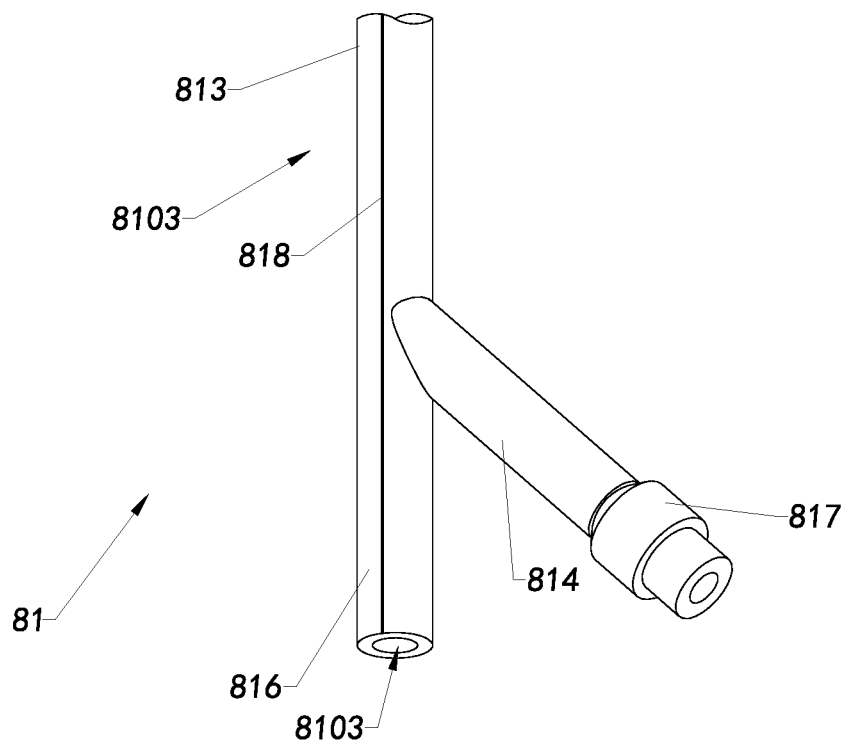
Figure 18:
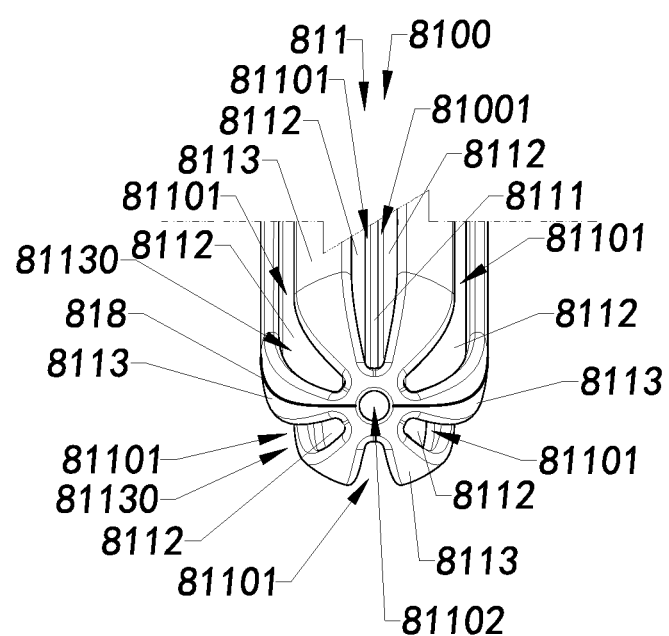
FIG. 18 is a schematic view of an end portion of the bending head of the nephrostomy tube with curved drainage according to the first referred embodiment of the present invention.
Figure 19A:
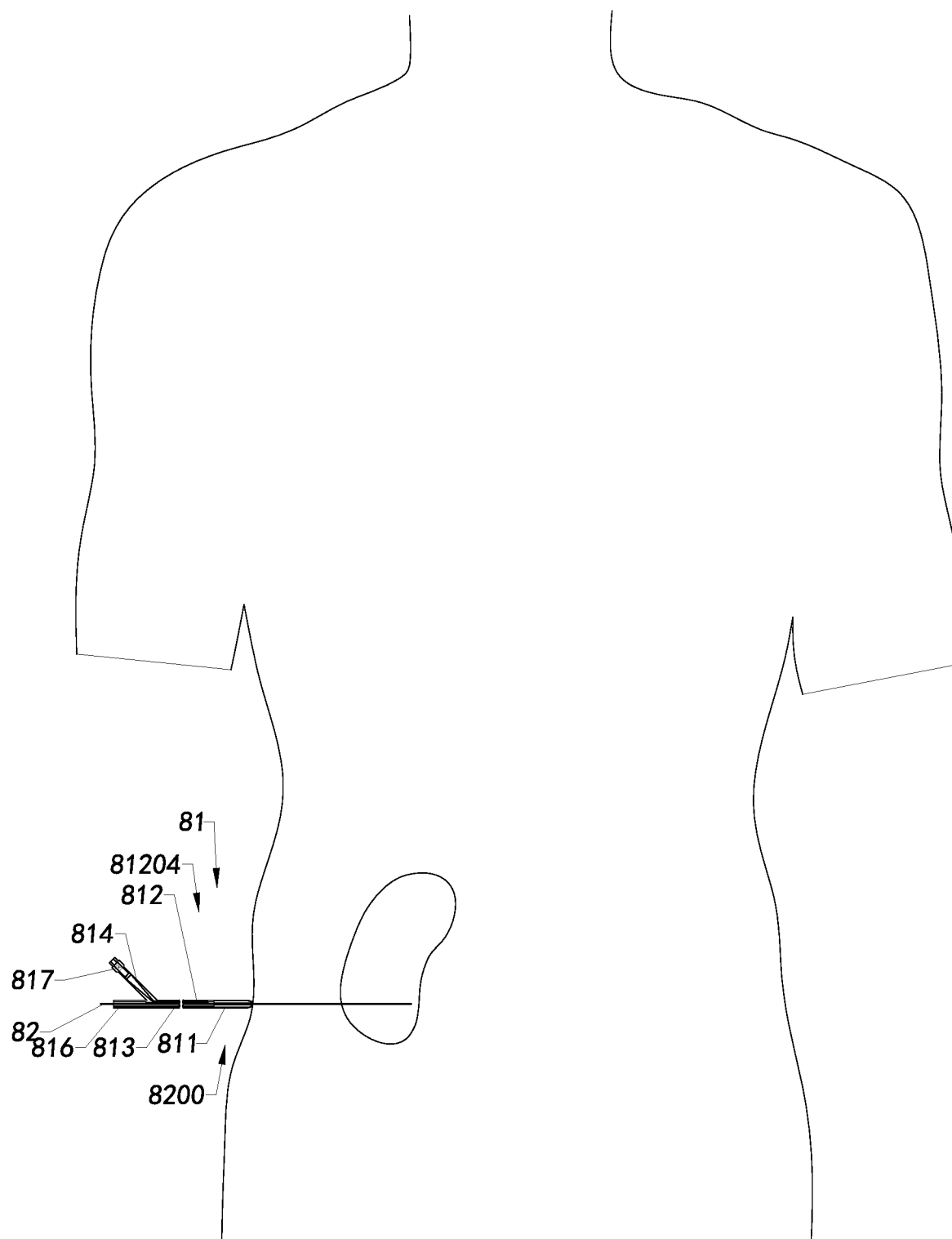
FIGS. 19A to 19E are schematic views illustrating the use of the nephrostomy tube with curved drainage according to the first referred embodiment of the present invention.
Figure 19B:
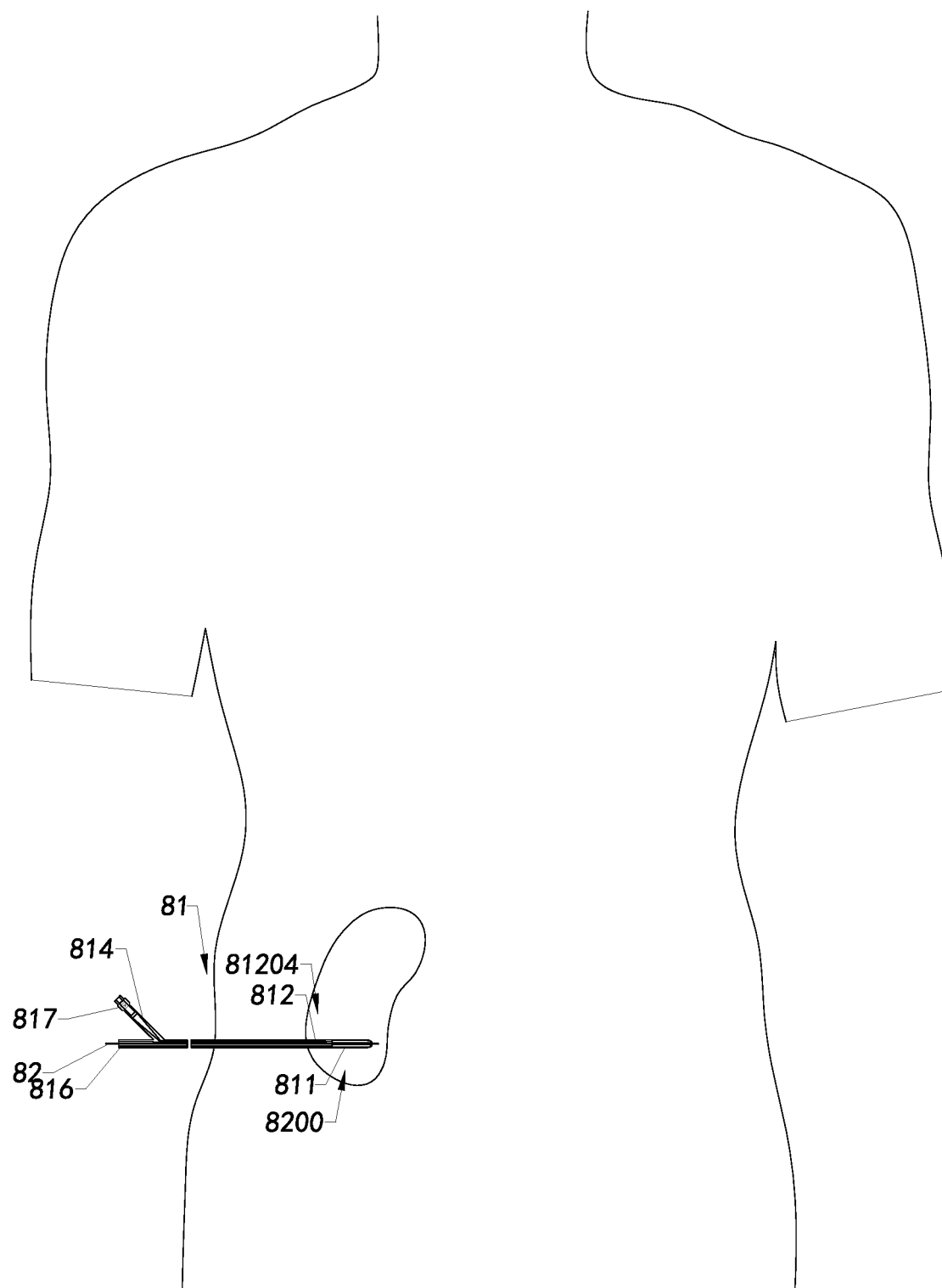
Figure 19C:
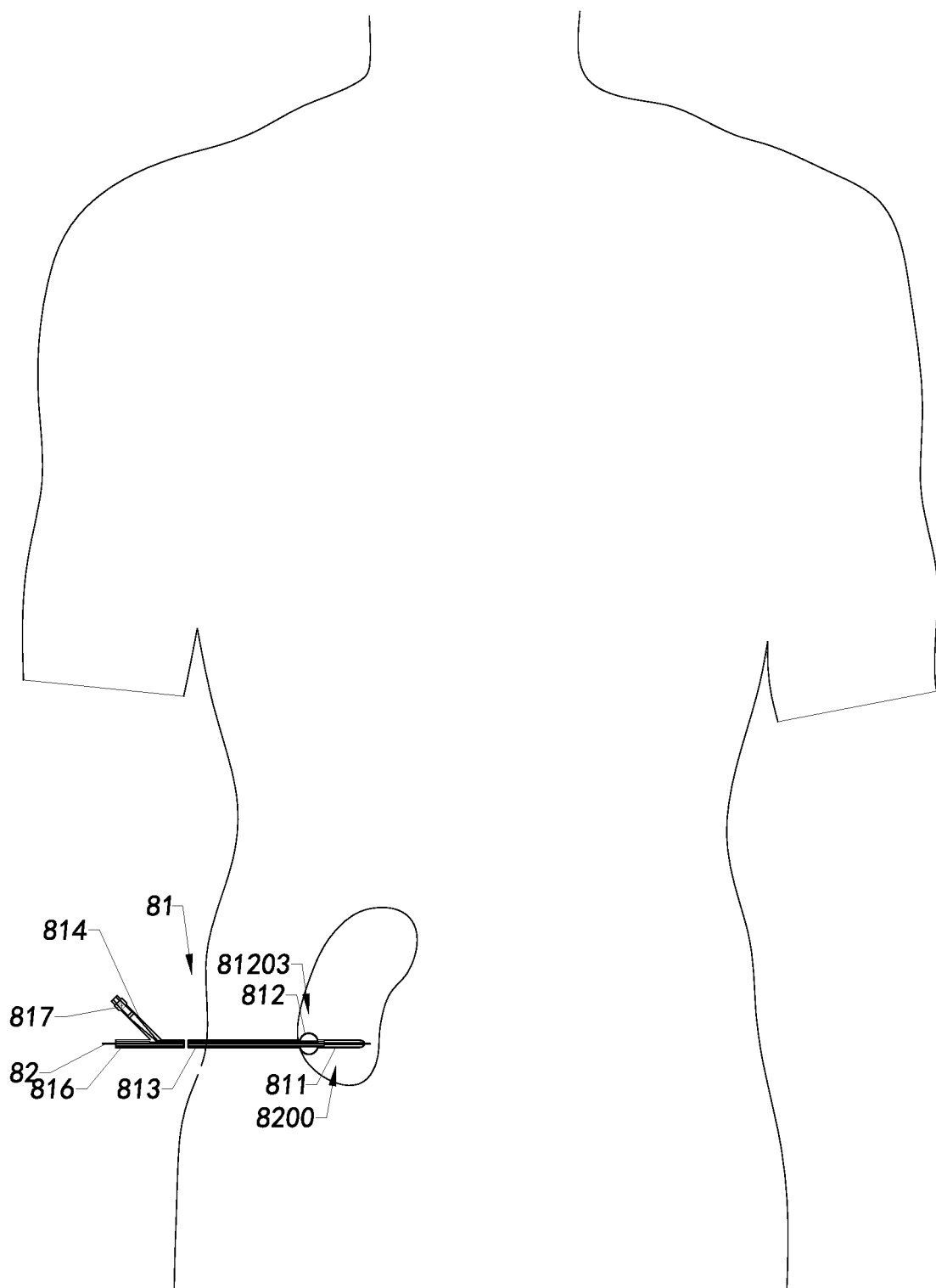
Figure 19D:
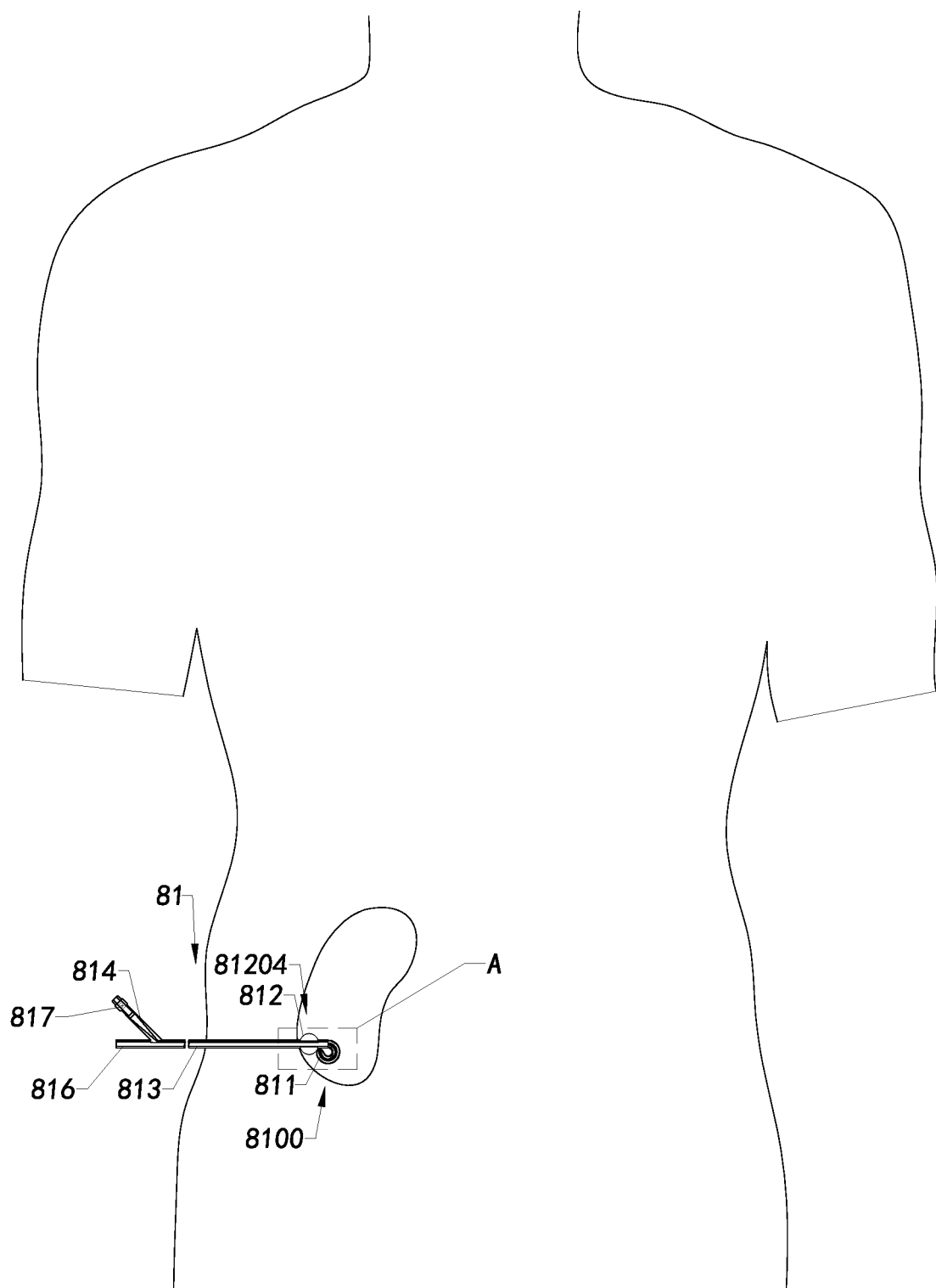
Figure 19E:
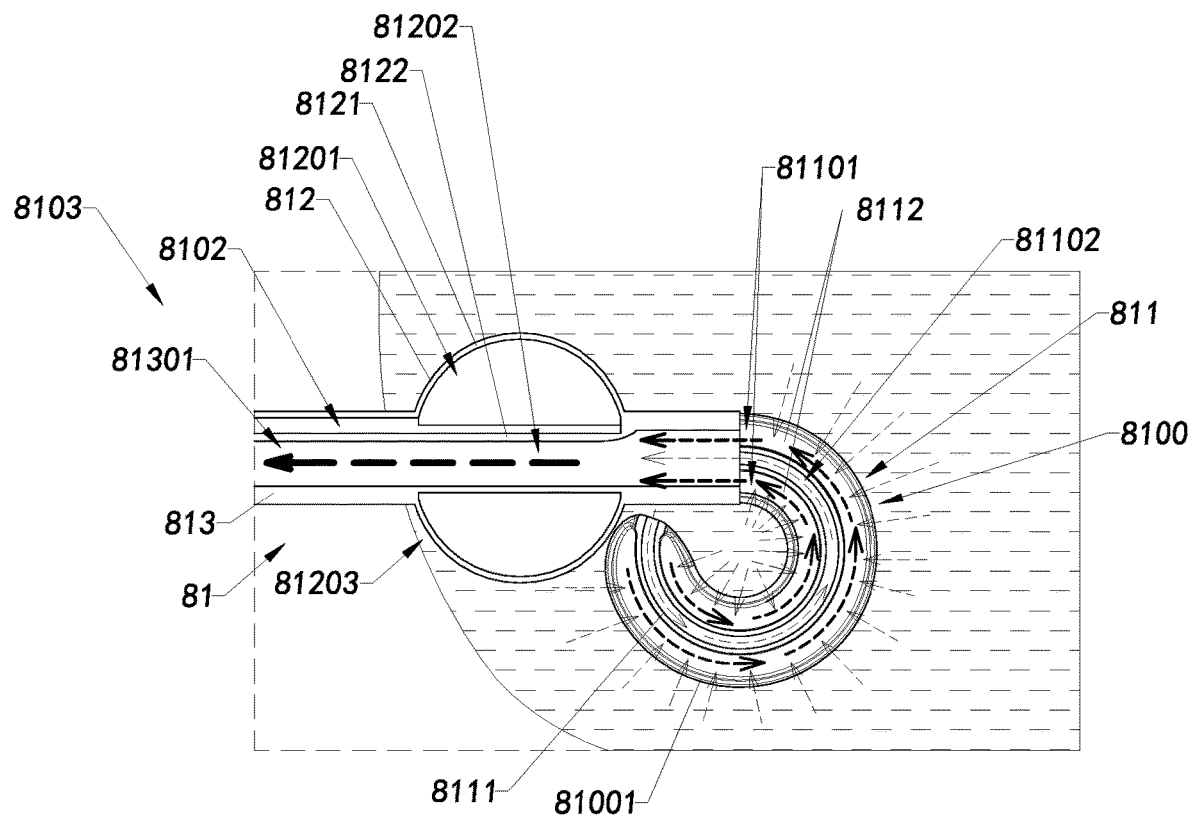

FIG. 13 is a schematic view that illustrates a nephrostomy tube with curved drainage at its bending sate according to a first preferred embodiment of the present invention. FIG. 14 is a schematic cross-sectional view of the nephrostomy tube with curved drainage shown in the FIG. 13. FIG. 15 is a schematic view that illustrates the nephrostomy tube with curved drainage at its stretched sate when being inserted with a guiding member. FIG. 16 is a partial enlarged schematic view of the nephrostomy tube with curved drainage according to the first referred embodiment of the present invention, illustrating the structure of the bending head. FIG. 17 is a schematic view of the nephrostomy tube with curved drainage at its inflated state. FIG. 18 is a schematic view of an end portion of the bending head of the nephrostomy tube with curved drainage according to the first referred embodiment of the present invention. FIGS. 19A to 19E are schematic views illustrating the use of the nephrostomy tube with curved drainage according to the first referred embodiment of the present invention.

Referring to the FIGS. 13 to 19E of the drawings, a nephrostomy tube with curved drainage 81 according to the present invention is illustrated, wherein the nephrostomy tube with curved drainage 81 is adapted for nephrostomy drainage surgery which includes but is not limited to the steps of puncturing or incising the kidney parenchyma, disposing the nephrostomy tube with curve drainage into the human body, and draining fluids such as urine, pus, and blood out of the body. For the purpose of easier illustration, the direction into the human's renal pelvis is defined as a front direction, while the direction out of the human's renal pelvis is defined as the rear direction.

The nephrostomy tube with curved drainage 81 has a bending state 8100 and a stretched state 8200, wherein in the bending state 8100, a front end potion of the nephrostomy tube with curved drainage 81 is bent and curved, while in the stretched state 8200, the nephrostomy tube with curved drainage 81 is stretched to get straight under the effect of a guiding member 82. In other words, when the nephrostomy tube with curved drainage 81 is required to be disposed into the renal pelvis through the human urethra passage, the nephrostomy tube with curved drainage 81 can be straightened under the effect of the guiding member 82 and then be inserted into the renal pelvis through an nephrostomy channel formed by puncturing or incising the kidney parenchyma, and after the nephrostomy tube with curved drainage 81 reaches into the renal pelvis, the guiding member 82 is adapted to be withdrawn and the end portion of the nephrostomy tube with curved drainage 81 returns to its bending state 8100 and gets curved. In other words, the front end portion of the nephrostomy tube with curved drainage 81 is resilient and bendable, which depends on the morphological requirements of the human body during use.

The guiding member 82 includes but is not limited to a guiding wire, an inner core, or other predetermined guiding element 82 that is able to cooperate with the nephrostomy tube with curved drainage 81. In other words, the shape and size of the guiding member 82 can be designed according to the size and shape of the nephrostomy tube with curved drainage 81 in actual manufacturing process, wherein if the shape and size requirements are consistent with the existing guiding wire or inner core, the existing guiding wires or inner core can be used for guiding, while if the shape and size requirements are not consistent, the guiding member 82 that cooperates with the nephrostomy tube with curved drainage 81 needs to be manufactured purposely.

The nephrostomy tube with curved drainage 81 comprises a bending head 811, a balloon element 812 and an elongated main body 813, wherein the bending head 811, the balloon element 812 and the elongated main body 813 are arranged in linearly in sequence. The bending head 811 is located in front of the balloon element 812, while the elongated main body 813 is located behind the balloon element 812. In other words, during use, the bending head 811 is the part that enters the human renal pelvis first, while the elongated main body 813 is the part that is adjacent to the external of the human body.

From the perspective of the relative positional relationship between the nephrostomy tube with curved drainage 81 and human organ parts when it is used, the bending head 811 is adapted for being disposed in the renal pelvis of the human body for drainage, the balloon element 812 is adapted for being mounted at the exiting port of the renal pelvis for affixing the nephrostomy tube with curved drainage 81 in the human body, while the balloon element 812 is adapted for being disposed along the urethra passage of the human's renal pelvis and for connecting to an external component. In other words, during use, the bending head 811 and the balloon element 812 are disposed in the renal pelvis, while the elongated main body 813 is disposed in the urethra passage and extended to the external. In this preferred embodiment, the external component includes but is not limited to urine bags and guiding tubes.

In terms of the function of each part of the nephrostomy tube with curved drainage 81, the bending head 811 is adapted for guiding fluid into the nephrostomy tube with curved drainage 81, that is, the bending head 811 is adapted for transferring the fluid in the human's renal pelvis to the external; the balloon element 812 is adapted for affixing the nephrostomy tube with curved drainage 81, more specifically, the balloon element 812 is adapted for affixing the nephrostomy tube with curved drainage 81 at the existing port of the human's renal pelvis; and the elongated main body 813 is adapted for transporting the fluid in the nephrostomy tube with curved drainage 81 outside, in other words, the elongated main body 813 is extended to the external along the nephrostomy channel for transporting the fluid in the nephrostomy tube with curved drainage 81 to the external along the nephrostomy channel.

In one embodiment of the present invention, the bending head 811, the balloon element 812 and the elongated main body 813 are integrally connected. For instance, when manufacturing the nephrostomy tube with curved drainage 81, one or more molding processes such as blow molding and injection molding can be performed in a molding apparatus to form the nephrostomy tube with curved drainage 81 which comprises the bending head 811, the balloon element 812 and the elongated main body 813. In another embodiment of the present invention, the bending head 811, the balloon element 812 and the elongated main body 813 can be detachably connected with one another.

The bending head 811, the balloon element 812 and the elongated main body 813 are linearly connected in a substantially flexible manner. More specifically, the bending head 811, the balloon element 812 and the elongated main body 813 are linearly arranged in order from the front to the rear, or from the top to the bottom.

In the bending state 8100, the bending head 811 is bent, while in the stretched state 8200, the bending head 811 straightened with the guidance of the guiding member 82. In other words, the guiding member 82 is adapted for controlling the shape of the bending head 811 from being bent to being straightened.

Furthermore, the end portion of the bending head 811 is tapering. More specifically, the longitudinal section of the end portion of the bending head 811 is substantially trapezoidal (while the sides of the trapezoid are arcs, that is, the outer size is smaller, the inner size is larger) or semi-elliptical, so as to facilitate the delivery of the nephrostomy tube with curved drainage 81 into the nephrostomy channel.

The nephrostomy tube with curved drainage 81 further comprises a positioning line 818 for identifying the position of the nephrostomy tube with curved drainage 81 in the human body and indicating the depth that the nephrostomy tube with curved drainage 81 being inserted into the human body. The positioning line 818 is visible under monitoring light such as B-ultrasound or X-ray, in other words, the positioning line 818 can be imaged and displayed under the B-ultrasound or X-ray, so as to determine the position and depth of the nephrostomy tube with curved drainage 81 to assist an operation such as inserting a tube by the medical staff.

The positioning line 818 is extended along the elongated main body 813, and in particular, the positioning line 818 is integrally configured inside the elongated main body 813. For instance, during the manufacture of the nephrostomy tube with curved drainage 81, the positioning line 818 is preset inside the elongated main body 813 when the elongated main body 813 is integrally formed. Furthermore, the positioning line 818 is integrally extended along the elongated main body 813, the balloon element 812 and the bending head 811, in other words, all of the elongated main body 813, the balloon element 812 and the bending head 811 have a portion of the elongated main body 813, such that entire of the nephrostomy tube with curved drainage 81 can be observed and position in the human body with the help of the positioning line 818.

Referring to the FIG. 14 of the drawings, the balloon element 812 comprises an outer wall 8121 and an inner wall 8122, wherein an air chamber 81201 is formed between the outer wall 8121 and the inner wall 8122. The inner wall 8122 has a circular structure to form a second inner channel 81202 therein, wherein the air chamber 81201 is circumferentially formed around the 81202. A portion of the positioning line 818 is integrally formed on the outer wall 8121.

The nephrostomy tube with curved drainage 81 has a guiding channel 8101 formed therein and extended from a front end of the nephrostomy tube with curved drainage 81 to a rear end thereof, for a guiding member 82 to pass through.

The balloon element 812 has an inflated state 81203 and an uninflated state 81204, wherein in the inflated state 81203, the balloon element 812 is inflated and expanded that the outer surface of the balloon element 812 is protruded from the outer surface of the elongated main body 813, while in the uninflated state 81204, the balloon element 812 is deflated and contracted that the outer surface of the balloon element 812 is substantially aligned with the outer surface of the elongated main body 813. In other words, in the inflated state 81203, the balloon element 812 is inflated to from an airbag that protrudes from the outer surface of the elongated main body 813.

The nephrostomy tube with curved drainage 81 comprises an inflating port 814 and an inflating channel 815 communicated with the inflating port 814, wherein the inflating channel 815 is extended along the elongated main body 813 to the balloon element 812. The balloon element 812 has an air chamber air chamber 81201 communicated with the inflating channel 815, such that air can be pumped into the air chamber 81201 through the inflating port 814 and the inflating channel 815, that is the airbag is formed by inflating the balloon element 812. In other words, the balloon element 812 can be inflated and uninflated through the inflating port 814 and the inflating channel 815.

In one embodiment of the present invention, the inflating channel 815 is formed by the inner wall of the nephrostomy tube with curved drainage 81, that is, the tubular body of the nephrostomy tube with curved drainage 81 is integrally coupled with the inner wall of the nephrostomy tube with curved drainage 81. In another embodiment of the present invention, the inflating channel 815 may be formed by an independent pipe member embedded in the inner wall of the elongated main body 813. The inflating port 814 is provided at the elongated main body 813 at a position adjacent to the external.

The bending head 811 has at least one drainage bending channel 81101, which has an opening 81001, wherein the drainage bending channel 81101 is communicated with the external through the opening 81001. The drainage bending channel 81101 is extended from an outer end of the bending head 811 towards the read end thereof to a predetermined position, and the drainage bending channel 81101 is longitudinally communicated with the balloon element 812. It is worth mentioning that since the bending head 811 is bent in its bending state 8100, in other words, the drainage bending channel 81101 is bent and curved accordingly to form a curved drainage path instead of a straight drainage, such that the probability of the accumulation of blood clots and other particulate matter can be minimized since there is no larger area of the plane or bearing surface. Accordingly, the opening 81001 of the drainage bending channel 81101 is extended along the bending head 811, that is, the opening 81001 of the drainage bending channel 81101 is facing towards the external in an elongated manner.

It is also worth mentioning that by means of the curved drainage method of the bending head 811, the transport path for the liquid in the body is extended while the entrance port for allowing the liquid flowing into the nephrostomy tube with curved drainage 81 is enlarged. In other words, the liquid may runs into the internal of the bending head 811 from any point of the drainage bending channel 81101, and then is transported along the drainage bending channel 81101 instead of being limited to any small hole at one position, thereby reducing the probability of blockage in a single position.

In this preferred embodiment of the present invention, the bending head 811 has a plurality of the drainage bending channels 81101, wherein the plurality of the drainage bending channels 81101 are arranged in a predetermined manner. For instance, the number of the drainage bending channel 81101 may be 2, 3, 3, 5, 6, 7, 8 or more.

More specifically, the bending head 811 in one embodiment of the present invention has six drainage bending channels 81101 centrally and symmetrically distributed about a center of the bending head 811.

Furthermore, in this preferred embodiment, the six drainage bending channels 81101 are evenly distributed along the peripheral edge of the bending head 811, that is, each of the drainage bending channels 81101 has a similar volume. In another embodiment of the present invention, the volumes of the six drainage bending channels 81101 may be different, and preferably, the volumes of the drainage bending channels 81101 are matched with the bending manner of the drainage bending channel 81101. For instance, the drainage bending channel 81101 located inside the bending head 811 has a relatively larger volume, while the drainage bending channel 81101 located on the outer side of the bending head 811 has a relatively smaller volume, that is, the opening of the drainage bending channel 81101 located inside the bending head bending head 811 is larger than the opening of the drainage bending channel 81101 located on the outer side of the bending head 811.

Referring to the FIGS. 14 and 16 of the drawings, the bending head 811 has a first inner channel 81102 for the guiding member 82 passing through. The first inner channel 81102 is approximately located at the center of the bending head 811 and is extended along the length direction of the bending head 811. Accordingly, the drainage bending channel 81101 is located outside of the first inner channel 81102. Furthermore, the drainage bending channel 81101 is circumferentially formed around the first inner channel 81102.

Referring to the FIG. 18 of the drawings, the outer ends of the plurality of the drainage bending channels 81101 are not communicated with the external directly, instead, the drainage bending channels 81101 are communicated to the external along its transverse and longitudinal directions. The end portion of the guiding wall 8112, which forms the drainage bending channel 81101, is extended in a radial manner for diverting the fluid entering from the end portion, and for separating bulky objects, such as blood clots.

In another preferred embodiment, the outer surface of the bending head 811 is configured in a closed conical structure, that is, the outer surface of the drainage bending channel 81101 is not communicated with the external, facilitating the bending head 811 extending into the nephrostomy channel when it is straightened.

Referring to the FIG. 14 of the drawings, the balloon element 812 has the air chamber 81201 and the second inner channel 81202, wherein the second inner channel 81202 circumferentially surrounds around the second inner channel 81202 to form the airbag in a ring-shaped or spherical-shaped. The air chamber 81201 is communicated with the inflating channel 815, such that air can be pumped into the air chamber 81201 through the inflating channel 815. And the inflating port 814 is communicated with the inflating channel 815. In other words, the inflating port 814, the inflating channel 815, and the air chamber 81201 are communicated with one another to form a charging channel 8102. During use of the nephrostomy tube with curved drainage 81 and after the balloon element 812 is disposed in a predetermined position in the renal pelvis, air can be pumped into the air chamber 81201 through the charging channel 8102 by an inflating apparatus such that the balloon element 812 is inflated and expanded to be affixed in the renal pelvis, wherein the inflated balloon element 812 is able to compress the bleeding position to stop bleeding. The nephrostomy tube with curved drainage 81 further comprises an air valve 817, detachably and sealingly coupled with the inflating port 814. After the balloon element 812 is inflated, the air valve 817 is adapted for sealing the inflating port 814 so as to maintain the balloon element 812 in its inflated state, and the air valve 817 is also adapted for releasing the air stored in the balloon element 812.

The second inner channel 81202 of the balloon element 812 is longitudinally communicated with the bending head 811 and the elongated main body 813. Furthermore, the second inner channel 81202 is communicated with the drainage bending channel 81101 and the first inner channel 81102 of the bending head 811.

In other words, the second inner channel 81202 is adapted for the guiding member 82 to pass through and for guiding the fluid in the human's renal pelvis. The second inner channel 81202, which is communicated with the first inner channel 81102 of the bending head 811, forms a portion of the guiding channel 8101. The second inner channel 81202 and the drainage bending channel 81101 of the bending head 811 form a portion of the transporting channel 8103.

During the use of the nephrostomy tube with curved drainage 81 and when the balloon element 812 is in its uninflated state 81204 and the bending head 811 is in its stretched state 8200 under the effect of the guiding member 82, the nephrostomy tube with curved drainage 81 is guided into the human's renal pelvis by the guiding member 82, and after the bending head 811 and the balloon element 812 reaches inside the human's renal pelvis, the balloon element 812 is inflated for maintaining the balloon element 812 in its inflated state 81203.

Referring the FIG. 14 of the drawing, the elongated main body 813 has a third inner channel 81301 which is longitudinally communicated with the second inner channel 81202. Overall, the drainage bending channel 81101 of the bending head 811, the second inner channel 81202 and the third inner channel 81301 are communicated with each other to form the guiding channel 8101. In other words, during the process of the guiding, the guiding member 82 penetrates through the third inner channel 81301, the second inner channel 81202 and the first inner channel 81102 in sequence, to make the bending head 811 to its stretched state 8200 and the entire 91 is straightened, such that the nephrostomy tube with curved drainage 81 can be inserted into the human's renal pelvis through the nephrostomy channel established during the surgery. When the nephrostomy tube with curved drainage 81 is put in use for drainage, the fluid in the human's renal pelvis is transported to the external through the drainage bending channel 81101, the second inner channel 81202, and the third inner channel 81301.

The elongated main body 813 further comprises an outlet port 816 which is adapted for connecting with external component, such as drain tube or urine bag. The size of the outlet port 816 is gradually increased from top of bottom, that is, the outer side of the outlet port 816 is larger than the inner side of the outlet port 816, to facilitate the sealing of the external drain tube or any other apparatus.

Referring to the FIG. 13 of the drawings, the bending head 811 comprises a first tubular body 8111 and a guiding wall 8112 radially extended from the 8111 to form the drainage bending channel 81101, wherein the guiding wall 8112 is longitudinally extended along the outer side of the first tubular body 8111. In other words, the space outside the first tubular body 8111 is divided by the guiding wall 8112 to form the drainage bending channels 81101, and the first tubular body 8111 forms the first inner channel 81102 therein. The rear end of the guiding wall 8112 is connected to the balloon element 812.

Referring to the FIGS. 14 and 16 of the drawings, the nephrostomy tube with curved drainage 81 further has at least one communication hole 81002 formed at the connection position of the bending head 811 and the balloon element 812, wherein the communication hole 81002 is communicated with the second inner channel 81202 of the balloon element 812. Furthermore, the communication hole 81002 is formed at the junction of two guiding walls 8112 and the balloon element 812. It is worth mentioning that the communication hole 81002 is located on the top of the balloon element 812, and formed by the end portion of the guiding wall 8112, that is, before entering the communication hole 81002, most of the fluid is guided gradually along the guiding wall 8112. Therefore, the guiding wall 8112 further has a certain conveying and filtering effect to prevent unwanted manner, such as blood clots, being blocked at the communication hole 81002.

The bending head 811 comprises a plurality of the guiding walls 8112 symmetrically distributed on the outside of the first tubular body 8111 to from the plurality of the drainage bending channels 81101. In this preferred embodiment, the bending head 811 comprises three guiding walls 8112 to form six drainage bending channels 81101, which are the first drainage bending channel, the second drainage bending channel, the third drainage bending channel, the fourth drainage bending channel, the fifth drainage bending channel, and the sixth drainage bending channel, from the inner side to the outer side of the bending head 811. The six drainage bending channels 81101 are communicated with the second inner channel 81202 independently and respectively.

It is worth mentioning that in one embodiment of the present invention, the plurality of the guiding walls 8112 and the first tubular body 8111 are integrally formed at one time during the manufacturing and molding process of the nephrostomy tube with curved drainage 81, that is, the first tubular body 8111 and the plurality of the guiding wall 8112 are integrally connected with each other at one time. In another embodiment of the present invention, the first tubular body 8111 is manufactured first and then the plurality of the guiding walls 8112 are formed on the outer side of the first tubular body 8111. One-piece molding method is preferred. It is worth mentioning that although the bending head 811 comprises six guiding walls 8112 and six drainage bending channels 81101 in this preferred embodiment, in other embodiments of the present invention, the bending head 811 may also includes other numbers of guiding walls 8112, such as 2, 3, 4, 5 or more, arranged in other ways, which is not intended to be limited in the present invention.

Furthermore, the bending head 811 further comprises at least a protective wall 8113 provided on the outer end of the guiding wall 8112, for preventing the end portion of the guiding wall 8112 from contacted with the external, i.e., for preventing the flat end portion of the guiding wall 8112 from contacting the inner membrane of human organs, causing adverse irritation or damaging the inner membrane.

Preferably, the protective wall 8113 is provided at the outer end of the guiding wall 8112 in an arc shape. In other embodiments of the present invention, the protective wall 8113 may also be configured in other shapes.

In this preferred embodiment of the present invention, the plurality of the protective walls 8113 is provided on the outer ends of the guiding walls 8112, that is, the number of the protective walls 8113 is matched with that of the guiding walls 8112. A gap 81130 is formed between each adjacent two protective walls 8113, wherein the gap 81130 is communicated with the drainage bending channel 81101 and the external space, in other words, each of the drainage bending channels 81101 is communicated with the external environment through each corresponding gap 81130.

The plurality of the protective walls 8113 are arranged at intervals, thereby forming a substantially annular outer surface, more specifically, a relatively flat arc-shaped surface as a whole, instead of a stripe-shaped partition surface formed by the end surface of the guide walls 8112. In other words, the protective walls 8113 are adapted for alleviating the stimulation of the guiding walls 8112. The protective wall 8113 covers the outside of the guiding walls 8112 in arc-shaped and each adjacent two protective walls 8113 defines the gap 81130 therebetween, in order to form a protective guide wall that tends to be circular under the premise of ensuring the passage of fluid.

In one embodiment of the present invention, the protective wall 8113 is extend from the two opposed side of the guiding wall 8112 in a substantially T-shape. In another embodiment of the present invention, the protective wall 8113 is extended at one side of the guiding wall 8112, that is, the protective wall 8113 and the guiding wall 8112 is configured in L-shaped, which is not intended to be limited in the present invention.

Referring to the FIG. 19A to 19E of the drawings, a use process of the nephrostomy tube with curved drainage 81 is illustrated, which comprises the following step. First, insert a guiding member 82 into the nephrostomy tube with curved drainage 81 to make the nephrostomy tube with curved drainage 81 into its stretched state 8200 that the bending head 811 is stretched and straightened. Then, guide the nephrostomy tube with curved drainage 81 into the renal pelvis through a nephrostomy channel by the guiding member 82. It is worth mentioning that the positioning line 818 is visible and positioned by an imaging device so as to determine the depth of the insertion of the nephrostomy tube with curved drainage 81. After the balloon element 812 of the nephrostomy tube with curved drainage 81 reaches the human's renal pelvis, a predetermined amount of air is inflated into the balloon element 812 by an inflating apparatus to make the nephrostomy tube with curved drainage 81. Then, pull out the guiding member 82 from the nephrostomy tube with curved drainage 81 to make the nephrostomy tube with curved drainage 81 into its bending state 8100, that the bending head 811 is naturally bent, and then the fluid in the renal pelvis is drained outwards by the nephrostomy tube with curved drainage 81. After the drainage is completed, insert the guiding member 82 into the nephrostomy tube with curved drainage 81 again to withdraw the nephrostomy tube with curved drainage 81 out of the human body.

Referring to the FIGS. 20A to 20E of the drawings, an alternative mode of the nephrostomy tube with curve drainage according to the first preferred embodiment of the present invention is illustrated.

Figure 20A:
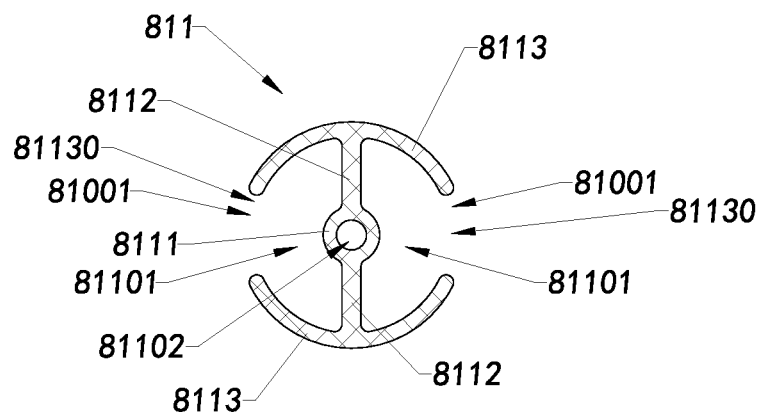
FIGS. 20A to 20E are schematic views illustrating the alternative modes of the nephrostomy tube with curved drainage of the first preferred embodiment of the present invention.

As shown in the FIG. 20A of the drawings, the nephrostomy tube with curved drainage 81 comprises two guiding walls 8112 provided at the two opposing sides of the first tubular body 8111, wherein the two guiding walls 8112 form two drainage bending channels 81101, each having an opening in a same size. Furthermore, viewed from the cross section, the two drainage bending channels 81101 are symmetrically provided at the two opposing sides of the two guiding walls 8112, wherein the protective walls 8113 are provided on the outer sides of the guiding wall 8112 respectively. Moreover, each adjacent two protective walls 8113 define a gap 81130 therebetween, which determines the size of the area that is adapted for communicating with the outside.

Figure 20B:
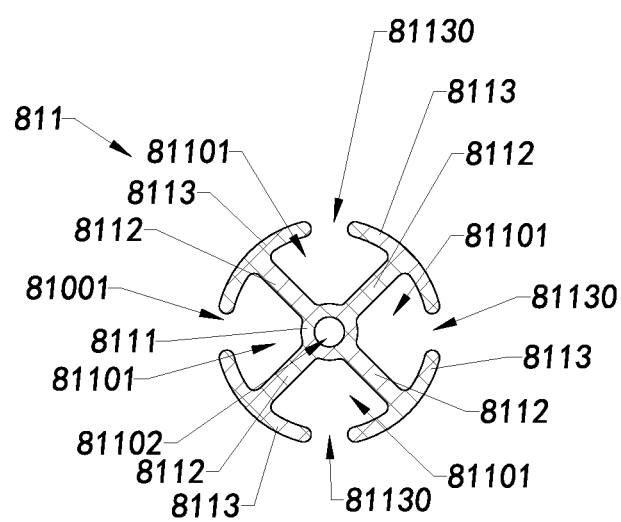

Referring to the FIG. 20B of the drawing, the nephrostomy tube with curved drainage 81 comprises four guiding walls 8112 provided at the outer side of the first tubular body 8111, wherein the four guiding walls 8112 form four drainage bending channels 81101, each having an opening in a same size. Furthermore, viewed from the cross section, the four drainage bending channels 81101 are symmetrically distributed around an axis of the first tubular body 8111, wherein the protective walls 8113 are provided on the outer sides of the guiding wall 8112 respectively. Moreover, each adjacent two protective walls 8113 define a gap 81130 therebetween, which determines the size of the area that is adapted for communicating with the outside.

Figure 20C:
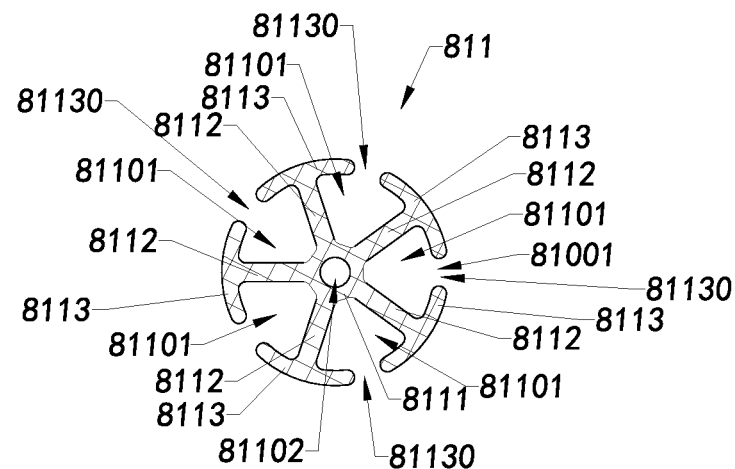

Referring to the FIG. 20C of the drawing, the nephrostomy tube with curved drainage 81 comprises five guiding walls 8112 provided at the outer side of the first tubular body 8111, wherein the five guiding walls 8112 form five drainage bending channels 81101, each having an opening in a same size. Furthermore, viewed from the cross section, the five drainage bending channels 81101 are symmetrically distributed around a center of the first tubular body 8111, wherein the protective walls 8113 are provided on the outer sides of the guiding wall 8112 respectively. Moreover, each adjacent two protective walls 8113 define a gap 81130 therebetween, which determines the size of the area that is adapted for communicating with the outside.

Figure 20D:
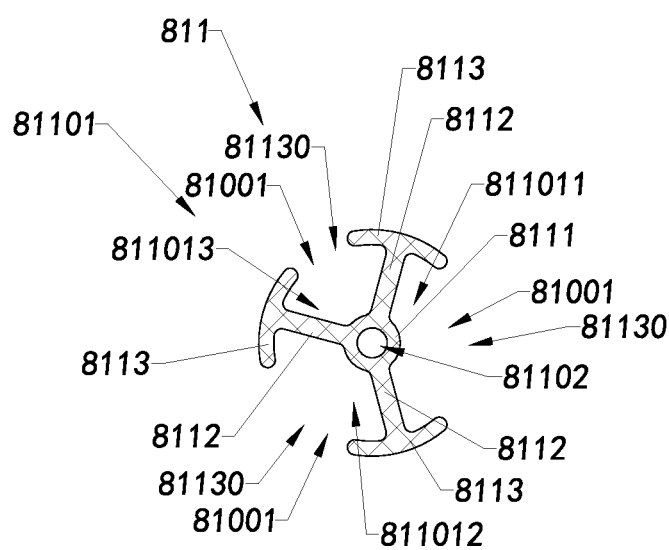

Referring to the FIG. 20D of the drawings, the nephrostomy tube with curved drainage 81 comprises three guiding walls 8112 provided at the outer side of the first tubular body 8111, wherein the three guiding walls 8112 form three drainage bending channels 81101, which are the first drainage bending channel 811011, the second drainage bending channel 811012, and the third drainage bending channel 811013. Each of the drainage bending channels 81101 has an opening in different sizes. Furthermore, the first drainage bending channel 811011 is located in the inner side of the bending head 811, the second drainage bending channel 811012 and the third drainage bending channel 811013 are adjacent to the outer side of the bending head 811. In this preferred embodiment, the size of the opening 81001 of the first drainage bending channel 811011 is greater than that of the communication hole 81002 of the second drainage bending channel 811012, wherein the size of the communication hole 81002 of the second drainage bending channel 811012 is greater than that of the communication hole 81002 of the third drainage bending channel 811013. In other words, the communication area between the drainage bending channel 81101 and the external can be adjusted by the inner size of the drainage bending channel 81101.

The protective walls 8113 are provided on the outer sides of the guiding wall 8112 respectively. Moreover, each adjacent two protective walls 8113 define a gap 81130 therebetween, which determines the size of the area that the drainage bending channel 81101 owns to communicate with the external. Accordingly, the size of the gap 81130 defined by the protective wall 8113 of the first drainage bending channel 811011, is greater than that of the gap 81130 defined by the protective wall 8113 of the second drainage bending channel 811012, while the size of the gap 81130 defined by the protective wall 8113 of the second drainage bending channel 811012 is greater than that of the gap 81130 defined by the protective wall 8113 of the third drainage bending channel 811013.

Figure 20E:
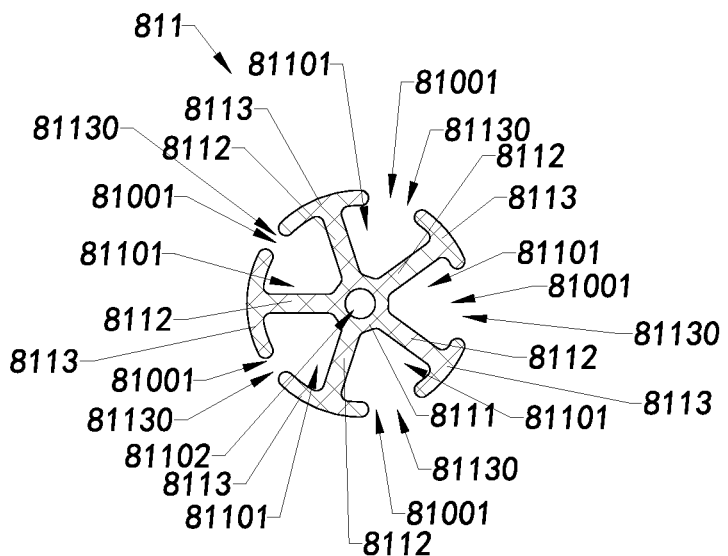

In the embodiment as shown in the FIG. 20E of the drawings, the size of the gap 81130 is adjusted by adjusting the width of the protective wall 8113, so as to adjust the size of the communication area of the drainage bending channel 81101 and the external.

In this preferred embodiment of the present invention, the nephrostomy tube with curved drainage 81 comprises five guiding walls 8112 provided at the outer side of the first tubular body 8111, wherein the five guiding walls 8112 form five drainage bending channels 81101, each having an opening in a same size. Furthermore, viewed from the cross section, the five drainage bending channels 81101 are symmetrically distributed around a center of the first tubular body 8111, wherein the protective walls 8113 are provided on the outer sides of the guiding wall 8112 respectively. Moreover, each adjacent two protective walls 8113 define a gap 81130 therebetween, which determines the size of the area that is adapted for communicating with the outside.

The right side and left side in the FIG. 20E correspond to the inner side and outer side of the nephrostomy tube with curved drainage 81 respectively, wherein the size of the gap 81130 defined by the drainage bending channel 81101, which is located in the inner side of the nephrostomy tube with curved drainage 81, is larger than that of the gap 81130 defined by the drainage bending channel 81101, which is located in the outer side of the nephrostomy tube with curved drainage 81, while the sizes of the gaps 81130 defined by the drainage bending channels 81101, which are located on the upper and lower sides of the nephrostomy tube with curved drainage 81. In other words, starting from the right side and in a clockwise direction, the five drainage bending channels 81101 are defined as the first drainage bending channel, the second drainage bending channel, the third drainage bending channel, the fourth drainage bending channel, and the fifth drainage bending channel, wherein the size of the gap 81130 defined by the first drainage bending channel is greater than that of the gap 81130 define by the second drainage bending channel, the size of the gap 81130 defined by the second drainage bending channel is greater than that of the gap 81130 defined by the third drainage bending channel, the size of the gap 81130 defined by the third drainage bending channel is equal to that of the gap 81130 defined by the fifth drainage bending channel, while the size of the gap 81130 defined by the third drainage bending channel is equal to that of the gap 81130 defined by the fourth drainage bending channel.

Figure 21A:
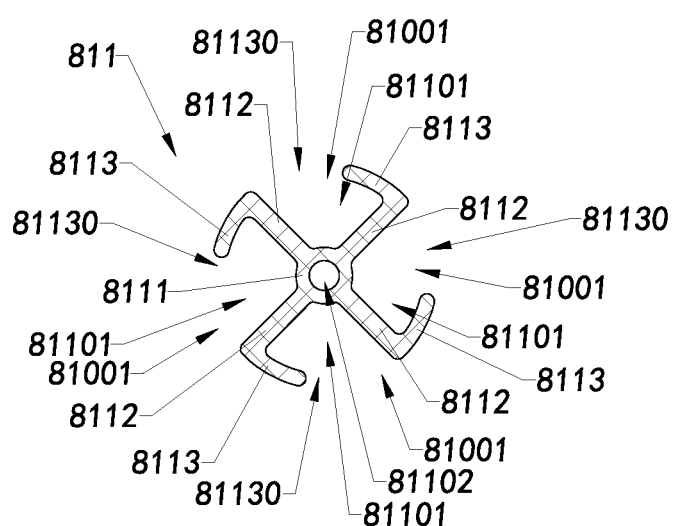
FIGS. 21A to 21C are schematic views illustrating the alternative modes of the protective wall of the nephrostomy tube with curved drainage according to a second preferred embodiment of the present invention.
Figure 21B:
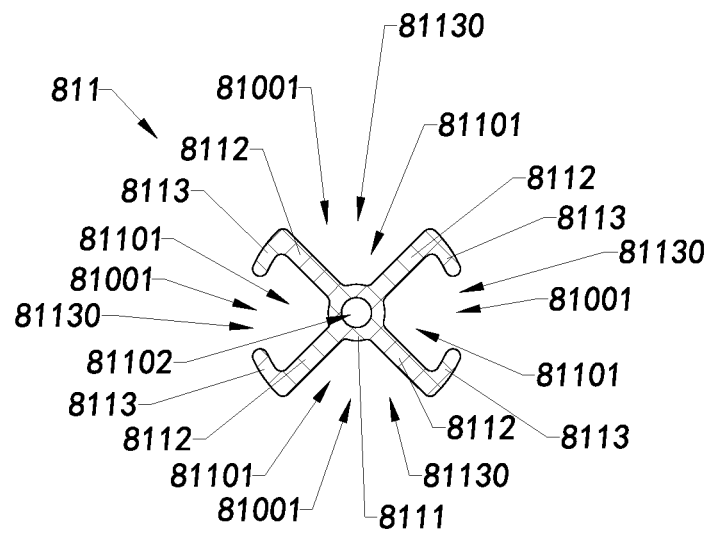

Referring to the FIGS. 21A and 21B of the drawings, an alternative mode of the protective wall of the bending head of the nephrostomy tube with curved drainage according to a second preferred embodiment of the present invention is illustrated.

Referring to the 21A of the drawings, the nephrostomy tube with curved drainage 81 comprises four guiding walls 8112 provided at the outer side of the first tubular body 8111, wherein the four guiding walls 8112 form four drainage bending channels 81101, each having an opening in a same size. Furthermore, viewed from the cross section, the four drainage bending channels 81101 are symmetrically distributed around an axis of the first tubular body 8111.

The protective walls 8113 are provided on the outer sides of the guiding wall 8112 respectively. Moreover, each adjacent two protective walls 8113 define a gap 81130 therebetween, which determines the size of the area that is adapted for communicating with the outside.

The protective wall 8113 is transversely or arcuately extended from an outer side of the guiding wall 8112, and the plurality of the protective walls 8113 are extended in the same direction, such as extended arcuately in a counter-clockwise direction, or extended arcuately in a clockwise direction, thereby forming the plurality of the gaps 81130 with the same size.

Referring to the 21B of the drawings, the nephrostomy tube with curved drainage 81 comprises four guiding walls 8112 provided at the outer side of the first tubular body 8111, wherein the four guiding walls 8112 form four drainage bending channels 81101, each having an opening in a same size. Furthermore, viewed from the cross section, the four drainage bending channels 81101 are symmetrically distributed around an axis of the first tubular body 8111.

The protective walls 8113 are provided on the outer sides of the guiding wall 8112 respectively, wherein each of the protective walls 8113 is extended in one single direction, that is, each of the protective walls 8113 is extending to one side of the guiding wall 8112, while two adjacent protective walls 8113 are extended in opposite directions, such that different openings and gaps are formed. Referring to the FIG. 21B of the drawings, from the right side in a clockwise direction, the horizontal first gap 81130 and the third gap 81130 have the same size, which are relatively small, and the first gap is symmetrical to the third gap, while the longitudinal second gap 81130 and the fourth gap 81130 have the same size, which are greater than those of the horizontal gaps.

Figure 21C:
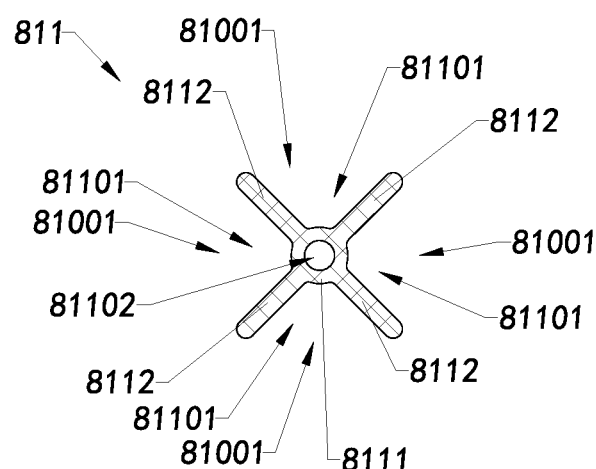

Referring to the FIG. 21C of the drawings, the nephrostomy tube with curved drainage 81 comprises four guiding walls 8112 provided at the outer side of the first tubular body 8111, wherein the four guiding walls 8112 form four drainage bending channels 81101, each having an opening in a same size. In particular, there is no protective wall 8113 provided in this preferred embodiment, that is, the drainage bending channel 81101 is communicated with the external through the openings 81001 directly.

Figure 22:
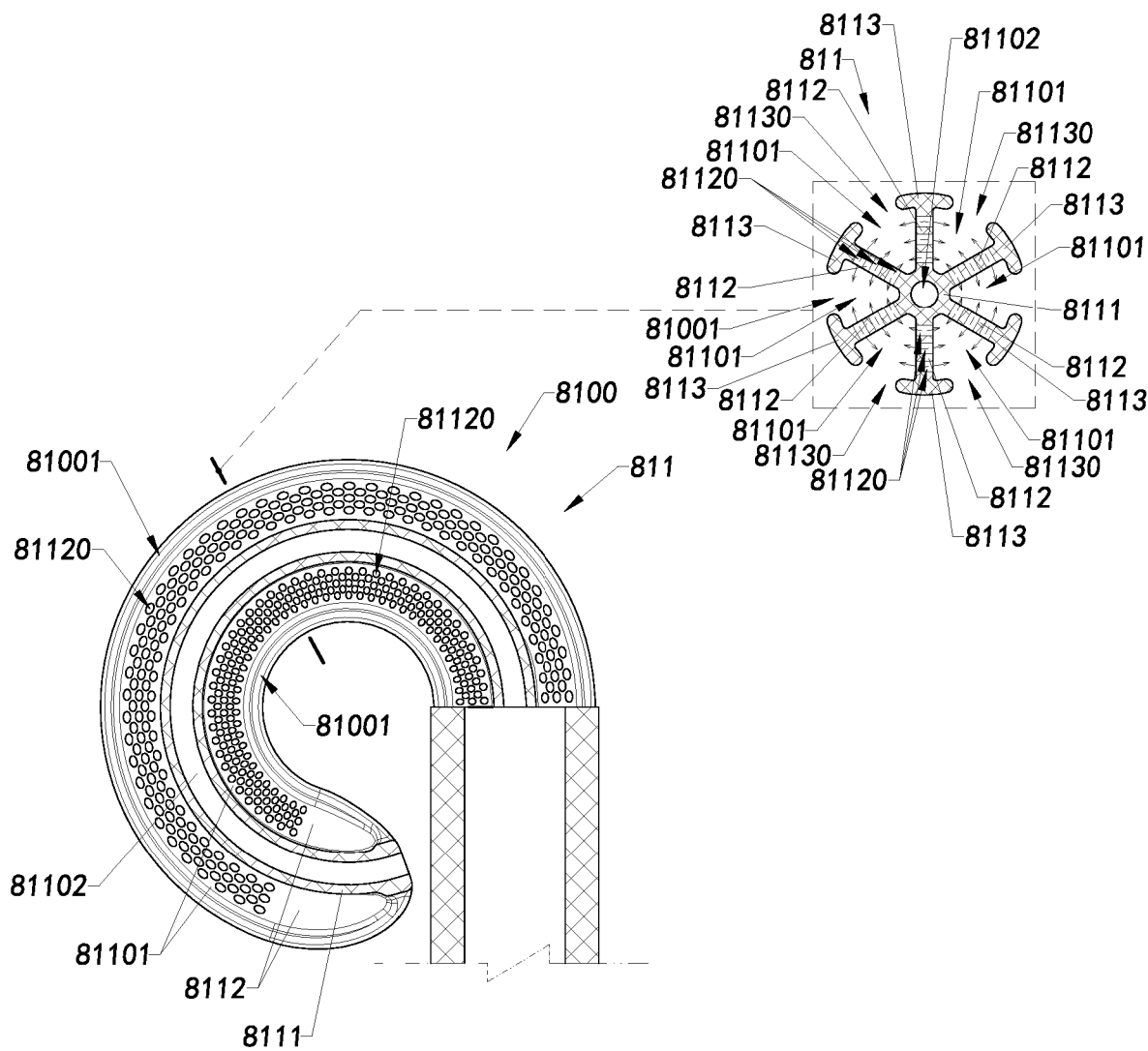
FIG. 22 is a schematic view illustrating a nephrostomy tube with curved drainage according to a third preferred embodiment of the present invention.

Referring to the FIG. 22 of the drawings, a nephrostomy tube with curved drainage according to a third preferred embodiment of the present invention is illustrated.

In this preferred embodiment, each of the guiding walls 8112 has at least one micro hole 81120, wherein the opposing two sides of the guiding wall 8112 is communicated via the micro hole 81120, in other words, the micro hole 81120 is a through hole that communicates the two adjacent drainage bending channels 81101.

It is worth mentioning that in this preferred embodiment, the plurality of the micro holes 81120 are arranged in a predetermined manner that micro holes 81120 communicate every two adjacent drainage bending channels 81101, such that the gas and the liquid within the two adjacent drainage bending channels 81101 can be communicated with each other. Therefore, the micro holes 81120 are capable of preventing a single drainage bending channel 81101 from being a closed space when it is blocked, that is, even if there is a blood clot in one of the drainage bending channels 81101, it will not adhere to the inner surface of the guiding wall 8112 due to the gas and the liquid within the drainage bending channel 81101 can run out of the drainage bending channel 81101 through the micro holes 81120.

In one embodiment of the present invention, the micro holes 81120 may be selectively formed on the guiding wall 8112, that is, not all the guiding wall 8112 need to be equipped with the micro hole 81120, while the number and the layout manner of the micro holes 81120 are not intended to be limited in the present invention.

The comparison of the effect of the conventional nephrostomy tube and the nephrostomy tube with curved drainage of the prevention invention is as follows.

A nephrostomy tube with curved drainage in 22F side model is manufactured by 3D printing, and a drainage test is performed between the nephrostomy tube with curved drainage of the present invention and the conventional nephrostomy tube in a same size model.

1. The Fluid to be Drained is Pure Water.

Two bottles of 350 ml of pure water are drained with a conventional nephrostomy tube in 22F size model and a nephrostomy tube with curved drainage in 22F size model of the present invention, wherein the drainage time of the conventional nephrostomy tube is 30 seconds, while the drainage time of the nephrostomy tube with curved drainage is 32 seconds.

2. The Fluid to be Drained is a Normal Saline with Blood Clots.

First, add 50 ml blood into 50 ml normal saline, and then let it stand for 15 minutes. The drainage experiment is not begun until blood clot is formed in the mixed fluid. The conventional nephrostomy tube in 22F size model is blocked by the blood clot within 5 second, and almost no fluid is drained out, while 50 ml of the mixed fluid is drained out in 26 seconds by the nephrostomy tube with curved drainage in 22F size model of the present invention.

Through the comparative experiments, it turns out that the drainage effect of the drainage nephrostomy tube for surgery of the present invention is equivalent to that of the ordinary nephrostomy tube of the same model in draining liquid, such as pure water. However, for mixed solutions containing coagulation, especially when there is a lot of coagulation, the ordinary silicone nephrostomy tube is easily blocked, while the drainage nephrostomy tube for surgery of the present invention has a better drainage effect and can prevent blockage to a certain extent. It is worth mentioning that the bending head 811 of the nephrostomy tube with curved drainage 81 of the present invention has the plurality of the drainage bending channels 81101, and the guiding walls 8112 that form the drainage bending channels 81101 are radially extended outwards. In other words, positions for drainage are formed on the entire circumferential surface and at different heights of the bending head 811, while the guiding walls 8112 have a certain supporting effect, such that when the blood clot reaches the end surfaces of the drainage bending channels 81101, it will be blocked such that it will not bock all the drainage areas of all the drainage bending channels 81101. In other words, the phenomenon of being completely blocked of the nephrostomy tube with curved drainage of the present invention will not occur, while the ordinary nephrostomy tube, because there are only two small holes that can be accessed, it is easy to be completely blocked by blood clots.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A nephrostomy tube assembly, comprising:
a mounting member; and
a nephrostomy tube for being guided into a human body by said mounting member, wherein said nephrostomy tube comprises:
a tubular main body having a drainage channel, wherein said tubular main body comprises a pillar member having an installation channel that is communicated to said drainage channel for the mounting member to pass therethrough, and a plurality of supporting walls spacedly and radially extended from said pillar member to define a plurality of guiding grooves each formed between two adjacent said supporting walls, wherein said tubular main body has a plurality of drainage inlets communicating said plurality of guiding grooves to said drainage channel respectively.

2. The nephrostomy tube assembly according to claim 1, wherein each of said guiding grooves has a drainage starting end and a drainage ending end which is opposite to said drainage starting end, wherein at least two said drainage starting ends are provided at different heights along said tubular main body.

3. The nephrostomy tube assembly according to claim 2, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves, wherein each of said plurality of protective walls is integrally extended from said corresponding supporting wall to form a shape selected from the group consisting of an arc shape, a substantially T-shaped configuration and a substantially L-shaped configuration.

4. The nephrostomy tube assembly according to claim 2, further comprising a marking line marked on said tubular main body.

5. The nephrostomy tube assembly according to claim 2, further comprising an air bag provided at an outer side of said drainage channel and having an air channel communicated with said air bag.

6. The nephrostomy tube assembly according to claim 1, wherein each of said guiding grooves has a drainage starting end and a drainage ending end which is opposite to said drainage starting end, wherein at least two said drainage ending ends are provided at different heights along said tubular main body.

7. The nephrostomy tube assembly according to claim 6, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves.

8. The nephrostomy tube assembly according to claim 1, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves.

9. The nephrostomy tube assembly according to claim 8, wherein each of said plurality of protective walls is integrally extended from said corresponding supporting wall to form a shape selected from the group consisting of an arc shape, a substantially T-shaped configuration and a substantially L-shaped configuration.

10. The nephrostomy tube assembly according to claim 1, wherein each of said plurality of supporting walls has at least one through hole which is communicated with two adjacent said guiding grooves.

11. A nephrostomy tube assembly, comprising:
a mounting member; and
a nephrostomy tube for being guided into a human body by said mounting member, wherein said nephrostomy tube comprises:
a tubular main body having a drainage channel, wherein said tubular main body comprises a curved bending portion which comprises a pillar member, and a plurality of supporting walls spacedly and radially extended from said pillar member to define a plurality of guiding grooves each curvedly formed between two adjacent said supporting walls, wherein said tubular main body has a plurality of drainage inlets communicating said plurality of guiding grooves to said drainage channel respectively, wherein said pillar member has an installation channel that is communicated to said drainage channel for said mounting member to pass therethrough, wherein said curved bending portion returns to a curved bending state when said mounting member is withdrawn from said tubular main body.

12. The nephrostomy tube assembly according to claim 11, wherein each of said guiding grooves has a drainage starting end and a drainage ending end which is opposite to said drainage starting end, wherein at least two said drainage ending ends are provided at different heights along said tubular main body.

13. The nephrostomy tube assembly according to claim 12, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves, wherein each of said plurality of protective walls is integrally extended from said corresponding supporting wall to form a shape selected from the group consisting of an arc shape, a substantially T-shaped configuration and a substantially L-shaped configuration.

14. The nephrostomy tube assembly according to claim 12, further comprising a marking line marked on said tubular main body.

15. The nephrostomy tube assembly according to claim 12, further comprising an air bag provided at an outer side of said drainage channel and having an air channel communicated with said air bag.

16. The nephrostomy tube assembly according to claim 11, wherein each of said guiding grooves has a drainage starting end and a drainage ending end which is opposite to said drainage starting end, wherein at least two said drainage starting ends are provided at different heights along said tubular main body.

17. The nephrostomy tube assembly according to claim 16, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves.

18. The nephrostomy tube assembly according to claim 11, wherein said tubular main body further comprises a plurality of protective walls transversely protruded from said plurality of supporting walls respectively to avoid stimulation on the human body by said plurality of supporting walls, wherein a gap is defined between each two adjacent said protective walls to communicate with each of said plurality of guiding grooves.

19. The nephrostomy tube assembly according to claim 18, wherein each of said plurality of protective walls is integrally extended from said corresponding supporting wall to form a shape selected from the group consisting of an arc shape, a substantially T-shaped configuration and a substantially L-shaped configuration.

20. The nephrostomy tube assembly according to claim 11, wherein each of said plurality of supporting walls has at least one through hole which is communicated with two adjacent said guiding grooves.

* * * * *